(12) United States Patent
Grossmann et al.

(10) Patent No.: US 7,098,241 B2
(45) Date of Patent: Aug. 29, 2006

(54) THIOPHENE HYDROXAMIC ACID DERIVATIVES

(75) Inventors: Adelbert Grossmann, Eglfing (DE); Frank Herting, Penzberg (DE); Matthias Koerner, Antdorf (DE); Klaus-Peter Kuenkele, Benediktbeuern (DE); Anja Limberg, Munich (DE); Olaf Mundigl, Weilheim (DE); Ulrich Tibes, Starnberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 424 days.

(21) Appl. No.: 10/732,633

(22) Filed: Dec. 10, 2003

(65) Prior Publication Data

US 2004/0122079 A1 Jun. 24, 2004

(30) Foreign Application Priority Data

Dec. 16, 2002 (EP) ............................ 02028038

(51) Int. Cl.
*A61K 31/38* (2006.01)
*C07D 333/22* (2006.01)

(52) U.S. Cl. .......................... 514/448; 549/72
(58) Field of Classification Search ............. 514/448; 549/72
See application file for complete search history.

(56) References Cited

U.S. PATENT DOCUMENTS

| 3,479,396 | A | 11/1969 | Nguyen et al. |
| 3,705,233 | A | 12/1972 | Lawrence et al. |
| 4,173,652 | A | 11/1979 | Bruins et al. |
| 4,769,461 | A | 9/1988 | Musser et al. |
| 5,087,743 | A | 2/1992 | Janssen et al. |
| 5,369,108 | A | 11/1994 | Breslow et al. |
| 5,438,052 | A | 8/1995 | Angehrn et al. |
| 5,700,811 | A | 12/1997 | Breslow et al. |
| 5,776,983 | A | 7/1998 | Washburn et al. |
| 5,786,358 | A | 7/1998 | Shih et al. |
| 6,008,257 | A | 12/1999 | Krüger et al. |
| 6,046,220 | A | 4/2000 | Bernardon |
| 6,392,010 | B1 | 5/2002 | Salvino et al. |
| 6,541,661 | B1 | 4/2003 | Delorme et al. |
| 6,660,728 | B1 * | 12/2003 | Scheunemann et al. ..... 514/183 |
| 6,747,057 | B1 * | 6/2004 | Ruzafa et al. .............. 514/446 |
| 6,784,173 | B1 * | 8/2004 | Leser-Reiff et al. ..... 514/231.5 |
| 2003/0073845 | A1 | 4/2003 | Barta et al. |

FOREIGN PATENT DOCUMENTS

| BE | 661226 | 9/1965 |
| DE | 2756216 | 6/1978 |
| EP | 133534 | 2/1985 |
| EP | 386452 | 9/1990 |
| EP | 447189 | 9/1991 |
| EP | 544166 | 6/1993 |
| EP | 761668 | 3/1997 |
| EP | 847992 | 6/1998 |
| JP | 54036229 | 3/1979 |
| JP | 57145838 | 9/1982 |
| JP | 57149254 | 9/1982 |
| JP | 01216961 | 8/1989 |
| JP | 03291264 | 12/1991 |
| JP | 04187666 | 7/1992 |
| JP | 04217950 | 8/1992 |
| JP | 10067682 | 3/1998 |
| JP | 10114654 | 5/1998 |
| JP | 10182583 | 7/1998 |
| JP | 10259176 | 9/1998 |
| JP | 10287634 | 10/1998 |
| WO | WO 89/05294 | 6/1989 |
| WO | 4402533 | 8/1995 |
| WO | WO 96/11902 | 4/1996 |
| WO | WO 96/32379 | 10/1996 |
| WO | WO 96/34851 | 11/1996 |
| WO | WO 97/12903 | 4/1997 |
| WO | WO 97/33856 | 9/1997 |
| WO | WO 98/05627 | 2/1998 |
| WO | WO 98/16514 | 4/1998 |
| WO | WO 98/32734 | 7/1998 |
| WO | WO 98/38163 | 9/1998 |
| WO | WO 98/57945 | 12/1998 |
| WO | WO 99/11606 | 3/1999 |
| WO | WO 99/12884 | 3/1999 |
| WO | WO 99/18076 | 4/1999 |
| WO | WO 99/19293 | 4/1999 |
| WO | WO 99/42436 | 8/1999 |
| WO | WO 01/38322 | 5/2001 |
| WO | WO 01/70675 | 9/2001 |

OTHER PUBLICATIONS

Abstract corresponding to WO 99/12884 (document B5), 1999.

(Continued)

*Primary Examiner*—Deborah C. Lambkin
(74) *Attorney, Agent, or Firm*—George W. Johnson; Patricia S. Rocha-Tramaloni

(57) ABSTRACT

The (R) and (S) enantiomers of a compound of formula I

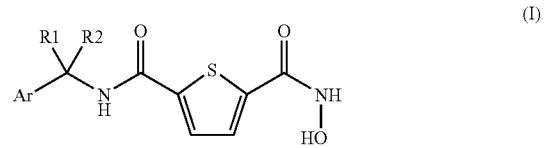

(I)

are novel antiproliferative therapeutic agents. These compounds have HDAC inhibitor activity and are useful in the treatment of cancer. Also disclosed are methods of making and using compounds of formula (I), as well as pharmaceutical compositions containing compounds of formula (I).

34 Claims, No Drawings

OTHER PUBLICATIONS

Abstract corresponding to JP 10287634 (document B8), 1998.
Abstract corresponding to JP 10259176 (document B9), 1998.
Abstract corresponding to JP 10182583 (document B11), 1998.
Abstract corresponding to JP 10114654 (document B12), 1998.
Abstract corresponding to JP 10067682 (document B14), 1998.
Abstract corresponding to JP 04217950 (document B24), 1992.
Abstract corresponding to JP 04187666 (document B25), 1992.
Abstract corresponding to JP 03291264 (document B26), 1991.
Abstract corresponding to JP 01216961 (document B29), 1989.
Abstract corresponding to JP 57145838 (document B32), 1982.
Abstract corresponding to JP 57149254 (document B33), 1982.
Abstract corresponding to JP 54036229 (document B34), 1979.
Sternson, S. M. et al, Organic Letters, vol. 3(26), (Dec. 2001) 4239-4242 XP002220922.

* cited by examiner

THIOPHENE HYDROXAMIC ACID DERIVATIVES

FIELD OF THE INVENTION

The present invention relates to novel (R)- and (S) enantiomers of thiophene hydroxamic acid derivatives, to a process for their manufacture, pharmaceutical compositions containing these compounds, and the use of these compounds to treatneoplasms of the hematopoetic and lymphatic system, in particular, solid tumors such as colon, breast, lung, prostate, rectal, stomach, bladder, pancreatic and ovarian tumors.

BACKGROUND OF THE INVENTION

The new compounds according to this invention are inhibitors of histone deacetylase (HDAC). Several structural classes of HDAC inhibitors have been identified and are reviewed in Marks, P. A., et al., J. Nat. Cancer Inst. 92 (2000) 1210–1216. More specifically, WO 98/55449, U.S. Pat. No. 5,369,108, WO 01/38322, WO 01/70675, and WO 02/22577 report alkanoyl, alkylenyl, alkenylenyl, benzyl, and cinnamyl hydroxamates with HDAC inhibitory activity.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490–1495).

SUMMARY OF THE INVENTION

We have now found that certain enantiomers of thiophene hydroxamic acid derivatives show improved anti-cell-proliferation activity and HDAC inhibitiory activity, and surprisingly show improved physicochemical- and pharmacokinetical properties such as better solubility and improved plasma stability.

In one embodiment, the present invention relates to new (R)- and (S) enantiomers of compounds of formula I

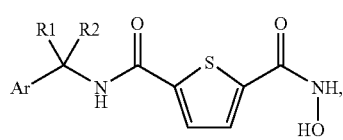

(I)

wherein $R^1$, $R^2$ and Ar are as defined below and the pharmaceutically acceptable salts of such compounds.

In another embodiment, the invention relates to a method of making of the above-mentioned compounds of formula (I).

In another embodiment, the invention relates to a method of treating cancer comprising administering an effective amount of a compound of the invention.

In another embodiment, the invention relates to pharmaceutical compositions containing a therapeutically effective amount of a compound of formula (I) and a pharmaceutically acceptable carrier or excipient.

DETAILED DESCRIPTION OF THE INVENTION

As used herein, the term "alkyl" means a straight-chain or branched-chain hydrocarbon group containing from 1 to 8, preferably from 1 to 6, carbon atoms, such as methyl, ethyl, n-propyl, isopropyl, n-butyl, iso-butyl, sec-butyl, t-butyl, n-pentyl, n-hexyl, n-heptyl as well as their isomers.

The term "alkenyl" means an unsaturated alkyl chain as defined above, containing one or two isolated double bonds, preferably one double bond. Examples are 1-propenyl, 2-propenyl, 1-butenyl, 2-butenyl, 1-pentenyl or 1-hexenyl.

The term "substituted", as in aryl is "substituted by", means that, unless otherwise indicated, the substitution can occur at one or more positions and that the substituents at each substitution site are independently selected from the specified options.

The term "aryl" as used herein denotes a phenyl or naphthyl, e.g. 1-naphthyl, 2-naphthyl or 3-naphthyl.

The term "heteroaryl" means a 5 to 10-membered, mono- or bicyclic aromatic ring which contains up to 3, preferably 1 or 2 heteroatoms selected independently from N, O or S and the remaining ring atoms being carbon atoms. Examples for such heteroaryl groups are thiophenyl, furyl, pyrrolyl, imidazolyl, pyridyl, pyrimidyl, pyrazinyl, pyridazinyl, triazinyl, thienyl, pyrazolyl, oxazolyl, isoxazolyl, thiazolyl, isothiazolyl, thiadiazolyl, oxadiazolyl, triazolyl, indolyl, quinolyl, isoquinolyl, benzofuranyl.

The term "halogen" as used herein denotes fluorine, chlorine, bromine or iodine.

In one embodiment the invention relates to (R)- and (S) enantiomers of formula (I),

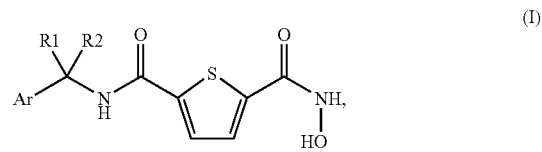

(I)

wherein
Ar is an aryl or heteroaryl group, each of which may be unsubstituted or substituted by up to three substituents selected from
halogen;
phenyl;
alkyl;
—O-alkyl;
—O-phenyl;
—O—(CH$_2$)$_n$—O—;
—OH;
—NO$_2$;
—NH$_2$;
—NH-alkyl;
—N(alkyl)$_2$;
—NH—C(O)-alkyl;

—SO₂alkyl;
—SO₂NH₂;
—SO₂NH-alkyl;
—SO₂N(alkyl)₂;
—C(O)—NH₂;
—C(O)—NH-alkyl;
—C(O)—N(alkyl)₂; or
—C(O)-alkyl;

R1 is hydrogen;
  phenyl; alkyl; or alkenyl; each of which may be unsubstituted or substituted by
    halogen,
    —OH,
    —NO₂,
    —NH₂,
    —O-alkyl,
    —O-aryl,
    —NH(alkyl),
    —N(alkyl)₂,
    morpholino,
    4-methylpiperazinyl, or
    aryl; or
  alternatively R1 together with the Ar-group forms a tetrahydronaphthalene-, indane- or dibenzosuberane ring;
R2 is hydrogen or alkyl; and
n is 1, 2 or 3;

or a physiologically acceptable salt thereof.

In a preferred embodiment, the invention relates to a compound of formula (I) wherein
Ar is an aryl or thiophen-2-yl group each of which may be unsubstituted or substituted by up to two substituents selected from
  halogen;
  phenyl;
  alkyl;
  —O-alkyl;
  —O—(CH₂)ₙ—O—;
  —OH;
  —NO₂;
  —NH₂;
  —NH-alkyl;
  —N(alkyl)₂;
  —NH—C(O)-alkyl;
  —SO₂alkyl;
  —SO₂NH₂;
  —SO₂NH-alkyl;
  —SO₂N(alkyl)₂;
  —C(O)—NH₂;
  —C(O)—NH-alkyl;
  —C(O)—N(alkyl)₂; or
  —C(O)-alkyl;
R1 is hydrogen;
  alkyl; or
  alkyl that is substituted by
    halogen;
    —OH;
    —NO₂;
    —NH₂;
    —O-alkyl;
    —O-aryl;
    —NH(alkyl);
    —N(alkyl)₂;
    morpholino;
    4-methylpiperazinyl; or
    aryl;
R2 is alkyl or hydrogen; and
n is 1, 2 or 3;

or a physiologically acceptable salt thereof.

Such (R) enantiomers are, for example:
(R)-thiophene-2,5-dicarboxylic acid 2-hydroxyamide 5-[(1-thiophen-2-yl-ethyl)-amide],
(R)-thiophene-2,5-dicarboxylic acid 2-hydroxyamide 5-{[1-(5-methyl-thiophen-2-yl)-ethyl]-amide}, or
(R)-thiophene-2,5-dicarboxylic acid 2-hydroxyamide 5-[(1-biphenyl-4-yl-ethyl)-amide].

Such (S) enantiomers are, for example:
(S)-thiophene-2,5-dicarboxylic acid 2-hydroxyamide 5-[(1-thiophen-2-yl-ethyl)-amide],
(S)-thiophene-2,5-dicarboxylic acid 2-hydroxyamide 5-{[1-(5-methyl-thiophen-2-yl)-ethyl]-amide}, or
(S)-thiophene-2,5-dicarboxylic acid 2-hydroxyamide 5-[(1-biphenyl-4-yl-ethyl)-amide].

Another preferred embodiment of the invention relates to (R)- and (S) enantiomers of formula I, wherein
Ar is phenyl substituted by one substituent selected from
  halogen;
  alkyl;
  —O-alkyl;
  —OH;
  —NH₂;
  —NH-alkyl;
  —N(alkyl)₂;
  —NH—C(O)-alkyl;
  —SO₂alkyl;
  —SO₂NH₂;
  —SO₂NH-alkyl;
  —SO₂N(alkyl)₂;
  —C(O)—NH₂;
  —C(O)—NH-alkyl;
  —C(O)—N(alkyl)₂; or
  —C(O)-alkyl;
R1 is hydrogen or alkyl; and
R2 is hydrogen;

or a physiologically acceptable salt thereof.

Such (R) enantiomers are for example:
(R)-thiophene-2,5-dicarboxylic acid 2-hydroxyamide 5-[(1-p-tolyl-ethyl)-amide],
(R)-thiophene-2,5-dicarboxylic acid 2-{[1-(4-fluoro-phenyl)-ethyl]-amide}5-hydroxyamide,
(R)-thiophene-2,5-dicarboxylic acid 2-{[1-(4-chloro-phenyl)-ethyl]-amide}5-hydroxyamide,
(R)-thiophene-2,5-dicarboxylic acid 2-{[1-(4-bromo-phenyl)-ethyl]-amide}5-hydroxyamide,
(R)-thiophene-2,5-dicarboxylic acid 2-hydroxyamide 5-{[1-(3-methoxy-phenyl)-ethyl]-amide},
(R)-thiophene-2,5-dicarboxylic acid 2-hydroxyamide 5-{[1-(4-methoxy-phenyl)-ethyl]-amide},
(R)-thiophene-2,5-dicarboxylic acid 2-hydroxyamide 5-{[1-(4-trifluoromethyl-phenyl)-ethyl]-amide},
(R)-thiophene-2,5-dicarboxylic acid 2-{[1-(4-tert-butyl-phenyl)-ethyl]-amide}5-hydroxyamide,
(R)-thiophene-2,5-dicarboxylic acid 2-hydroxyamide 5-{[1-(4-methanesulfonyl-phenyl)-ethyl]-amide},
(R)-thiophene-2,5-dicarboxylic acid 2-{[1-(3-amino-phenyl)-ethyl]-amide}5-hydroxyamide,
(R)-thiophene-2,5-dicarboxylic acid 2-{[1-(2-amino-phenyl)-ethyl]-amide}5-hydroxyamide,
(R)-thiophene-2,5-dicarboxylic acid 2-{[1-(4-ethyl-phenyl)-ethyl]-amide}5-hydroxyamide,
(R)-thiophene-2,5-dicarboxylic acid 2-{[1-(4-ethoxy-phenyl)-ethyl]-amide}5-hydroxyamide, (R)-thiophene-2,5-dicarboxylic acid 2-{[1-(4-carbamoyl-phenyl)-ethyl]-amide}5-hydroxyamide, or
(R)-thiophene-2,5-dicarboxylic acid 2-hydroxyamide 5-({1-[4-(3-methyl-butylcarbamoyl)-phenyl]-ethyl}-amide).

Such (S) enantiomers are, for example:
(S)-thiophene-2,5-dicarboxylic acid 2-hydroxyamide 5-[(1-p-tolyl-ethyl)-amide],
(S)-thiophene-2,5-dicarboxylic acid 2-{[1-(4-fluoro-phenyl)-ethyl]-amide}5-hydroxyamide,
(S)-thiophene-2,5-dicarboxylic acid 2-{[1-(4-chloro-phenyl)-ethyl]-amide}5-hydroxyamide,
(S)-thiophene-2,5-dicarboxylic acid 2-{[1-(4-bromo-phenyl)-ethyl]-amide}5-hydroxyamide,
(S)-thiophene-2,5-dicarboxylic acid 2-hydroxyamide 5-{[1-(3-methoxy-phenyl)-ethyl]-amide},
(S)-thiophene-2,5-dicarboxylic acid 2-hydroxyamide 5-{[1-(4-methoxy-phenyl)-ethyl]-amide},
(S)-thiophene-2,5-dicarboxylic acid 2-hydroxyamide 5-{[1-(4-trifluoromethyl-phenyl)-ethyl]-amide},
(S)-thiophene-2,5-dicarboxylic acid 2-{[1-(4-tert-butyl-phenyl)-ethyl]-amide}5-hydroxyamide,
(S)-thiophene-2,5-dicarboxylic acid 2-hydroxyamide 5-{[1-(4-methanesulfonyl-phenyl)-ethyl]-amide},
(S)-thiophene-2,5-dicarboxylic acid 2-{[1-(3-amino-phenyl)-ethyl]-amide}5-hydroxyamide,
(S)-thiophene-2,5-dicarboxylic acid 2-{[1-(2-amino-phenyl)-ethyl]-amide}5-hydroxyamide,
(S)-thiophene-2,5-dicarboxylic acid 2-{[1-(4-ethyl-phenyl)-ethyl]-amide}5-hydroxyamide,
(S)-thiophene-2,5-dicarboxylic acid 2-{[1-(4-ethoxy-phenyl)-ethyl]-amide}5-hydroxyamide,
(S)-thiophene-2,5-dicarboxylic acid 2-{[1-(4-carbamoyl-phenyl)-ethyl]-amide}5-hydroxyamide, or
(S)-thiophene-2,5-dicarboxylic acid 2-hydroxyamide 5-({1-[4-(3-methyl-butylcarbamoyl)-phenyl]-ethyl}-amide).

Yet another preferred embodiment of the invention relates to (R)- and (S) enantiomers of formula I, wherein
Ar is phenyl;
R1 is phenyl;
  alkyl; or
  alkyl substituted by
    halogen;
    —OH;
    —NH$_2$;
    —O-alkyl;
    —O-aryl;
    —NH(alkyl);
    —N(alkyl)$_2$;
    morpholinyl;
    4-methylpiperazinyl; or
    phenyl; and
R2 is hydrogen or alkyl;

or a physiologically acceptable salt thereof.

Such (R) enantiomers are, for example:
(R)-thiophene-2,5-dicarboxylic acid 2-hydroxyamide 5-[(1-phenyl-ethyl)-amide],
(R)-thiophene-2,5-dicarboxylic acid 2-hydroxyamide 5-[(1-phenyl-propyl)-amide,]
(R)-thiophene-2,5-dicarboxylic acid 2-hydroxyamide 5-[(2-hydroxy-1-phenyl-ethyl)-amide],
(R)-thiophene-2,5-dicarboxylic acid 2-hydroxyamide 5-[(3-hydroxy-1-phenyl-propyl)-amide,]
(R)-thiophene-2,5-dicarboxylic acid 2-hydroxyamide 5-[(2-methoxy-1-phenyl-ethyl)-amide],
(R)-thiophene-2,5-dicarboxylic acid 2-[(2-dimethylamino-1-phenyl-ethyl)-amide]5-hydroxyamide,
(R)-thiophene-2,5-dicarboxylic acid 2-hydroxyamide 5-[(1-phenyl-2-pyrrolidin-1-yl-ethyl)-amide],
(R)-thiophene-2,5-dicarboxylic acid 2-hydroxyamide 5-[(2-morpholin-4-yl-1-phenyl-ethyl)-amide],
(R)-thiophene-2,5-dicarboxylic acid 2-[(1,2-diphenyl-ethyl)-amide]5-hydroxyamide,
(R)-thiophene-2,5-dicarboxylic acid 2-hydroxyamide 5-[(1-phenyl-pentyl)-amide],
(R)-thiophene-2,5-dicarboxylic acid 2-hydroxyamide 5-[(1-phenyl-butyl)-amide],
(R)-thiophene-2,5-dicarboxylic acid 2-hydroxyamide 5-[(2-methyl-1-phenyl-propyl)-amide], or
(R)-thiophene-2,5-dicarboxylic acid 2-hydroxyamide 5-[(3-methyl-1-phenyl-butyl)-amide].

Such (S) enantiomers are, for example:
(S)-thiophene-2,5-dicarboxylic acid 2-hydroxyamide 5-[(1-phenyl-ethyl)-amide],
(S)-thiophene-2,5-dicarboxylic acid 2-hydroxyamide 5-[(1-phenyl-propyl)-amide],
(S)-thiophene-2,5-dicarboxylic acid 2-hydroxyamide 5-[(2-hydroxy-1-phenyl-ethyl)-amide],
(S)-thiophene-2,5-dicarboxylic acid 2-hydroxyamide 5-[(3-hydroxy-1-phenyl-propyl)-amide],
(S)-thiophene-2,5-dicarboxylic acid 2-hydroxyamide 5-[(2-methoxy-1-phenyl-ethyl)-amide],
(S)-thiophene-2,5-dicarboxylic acid 2-[(2-dimethylamino-1-phenyl-ethyl)-amide]5-hydroxyamide,
(S)-thiophene-2,5-dicarboxylic acid 2-hydroxyamide 5-[(1-phenyl-2-pyrrolidin-1-yl-ethyl)-amide],
(S)-thiophene-2,5-dicarboxylic acid 2-hydroxyamide 5-[(2-morpholin-4-yl-1-phenyl-ethyl)-amide],
(S)-thiophene-2,5-dicarboxylic acid 2-[(1,2-diphenyl-ethyl)-amide]5-hydroxyamide,
(S)-thiophene-2,5-dicarboxylic acid 2-hydroxyamide 5-[(1-phenyl-pentyl)-amide],
(S)-thiophene-2,5-dicarboxylic acid 2-hydroxyamide 5-[(1-phenyl-butyl)-amide],
(S)-thiophene-2,5-dicarboxylic acid 2-hydroxyamide 5-[(2-methyl-1-phenyl-propyl)-amide], or
(S)-thiophene-2,5-dicarboxylic acid 2-hydroxyamide 5-[(3-methyl-1-phenyl-butyl)-amide].

Yet another preferred embodiment of the invention relates to (R)- and (S) enantiomers of formula I, wherein
Ar is naphthyl; and
R1 and R2 are independently selected from
  hydrogen;
  alkyl- or alkenyl, each of which may be unsubstituted or substituted by
    alkyl;
    halogen;
    —OH;
    —NO$_2$;
    —NH$_2$;
    —O-alkyl;
    —O-aryl;
    —NH(alkyl);
    —N(alkyl)$_2$;

or a physiologically acceptable salt thereof.

Such (R) enantiomers are, for example:
(R)-thiophene-2,5-dicarboxylic acid 2-hydroxyamide 5-[(1-naphthalen-1-yl-ethyl)-amide],
(R)-thiophene-2,5-dicarboxylic acid 2-hydroxyamide 5-[(1-naphthalen-2-yl-ethyl)-amide].

Such (S)-enantiomers are, for example:

(S)-thiophene-2,5-dicarboxylic acid 2-hydroxyamide 5-[(1-naphthalen-1-yl-ethyl)-amide],
(S)-thiophene-2,5-dicarboxylic acid 2-hydroxyamide 5-[(1-naphthalen-2-yl-ethyl)-amide].

Yet another preferred embodiment of the invention relates to (R)- and (S) enantiomers of formula I, wherein
Ar and R1 together form tetrahydronaphthalenyl; indanyl; or dibenzosuberanyl, each of which optionally may be substituted by
alkyl;
halogen;
—OH;
—NO$_2$;
—NH$_2$;
—O-alkyl;
—O-aryl;
—NH(alkyl);
—N(alkyl)$_2$; and
R2 is hydrogen;

or a physiologically acceptable salt thereof.
Such (R)-enantiomers are, for example:
(R)-thiophene-2,5-dicarboxylic acid 2-hydroxyamide 5-indan-1-ylamide,
(R)-thiophene-2,5-dicarboxylic acid 2-hydroxyamide 5-[(1,2,3,4-tetrahydro-naphthalen-1-yl)-amide].
Such (S)-enantiomers are, for example:
(S)-thiophene-2,5-dicarboxylic acid 2-hydroxyamide 5-indan-1-ylamide,
(S)-thiophene-2,5-dicarboxylic acid 2-hydroxyamide 5-[(1,2,3,4-tetrahydro-naphthalen-1-yl)-amide].

Still another preferred embodiment of the invention relates to (R)- and (S) enantiomers of formula I, wherein
Ar is a heteroaryl group which may be unsubstituted or substituted by up to three substituents selected from
halogen;
phenyl;
alkyl;
—O-alkyl;
—O-phenyl;
—O—(CH$_2$)$_n$—O—;
—OH;
—NO$_2$;
—NH$_2$;
—NH-alkyl;
—N(alkyl)$_2$;
—NH—C(O)-alkyl;
—SO$_2$alkyl;
—SO$_2$NH$_2$;
—SO$_2$NH-alkyl;
—SO$_2$N(alkyl)$_2$;
—C(O)—NH$_2$;
—C(O)—NH-alkyl;
—C(O)—N(alkyl)$_2$; or
—C(O)-alkyl;
R1 is hydrogen; or
phenyl; alkyl; or alkenyl; each of which may be unsubstituted or substituted by
halogen;
—OH;
—NO$_2$;
—NH$_2$;
—O-alkyl;
—O-aryl;
—NH(alkyl);
—N(alkyl)$_2$;
morpholino;
4-methylpiperazinyl; or
aryl; or
alternatively, R1 together with the Ar-group forms a tetrahydronaphthalene-, indane- or dibenzosuberane ring;
R2 is hydrogen or alkyl; and
n is 1, 2 or 3;

or a physiologically acceptable salt thereof.
Still another preferred embodiment of the invention relates to (R)- and (S) enantiomers of formula I, wherein
Ar is a heteroaryl group that may be unsubstituted or substituted by up to three substituents selected from
halogen;
phenyl;
alkyl;
—O-alkyl;
—O-phenyl;
—O—(CH$_2$)$_n$—O—;
—OH;
—NO$_2$;
—NH$_2$;
—NH-alkyl;
—N(alkyl)$_2$;
—NH—C(O)-alkyl;
—SO$_2$alkyl;
—SO$_2$NH$_2$;
—SO$_2$NH-alkyl;
—SO$_2$N(alkyl)$_2$;
—C(O)—NH$_2$;
—C(O)—NH-alkyl;
—C(O)—N(alkyl)$_2$; or
—C(O)-alkyl;
R1 is hydrogen;
R2 is alkyl; and
n is 1, 2 or 3;

or a physiologically acceptable salt thereof
Yet another preferred embodiment of the invention relates to (R)- and (S) enantiomers of formula I, wherein
Ar is benzofuran-2-yl,
isoxazol-3-yl,
pyridin-2-yl,
pyridin-3-yl,
pyridin-4-yl,
furan-2-yl, or
pyrrol-3-yl, each of which may be unsubstituted or substituted by up to two substituents selected from phenyl or alkyl;
R1 is hydrogen; and
R2 is alkyl;

or a physiologically acceptable salt thereof.
Such (R)-enantiomers are, for example:
(R)-thiophene-2,5-dicarboxylic acid 2-[(1-benzofuran-2-yl-ethyl)-amide]5-hydroxyamide,
(R)-thiophene-2,5-dicarboxylic acid 2-hydroxyamide 5-{[1-(5-phenyl-isoxazol-3-yl)-ethyl]-amide},
(R)-thiophene-2,5-dicarboxylic acid 2-hydroxyamide 5-[(1-pyridin-2-yl-ethyl)-amide],
(R)-thiophene-2,5-dicarboxylic acid 2-hydroxyamide 5-[(1-furan-2-yl-ethyl)-amide],
(R)-thiophene-2,5-dicarboxylic acid 2-hydroxyamide 5-[(1-pyridin-3-yl-ethyl)-amide],
(R)-thiophene-2,5-dicarboxylic acid 2-hydroxyamide 5-{[1-(1-methyl-1H-pyrrol-3-yl)-ethyl]-amide}, or (R)-thiophene-2,5-dicarboxylic acid 2-hydroxyamide 5-[(1-pyridin-4-yl-ethyl)-amide].

Such (S)-enantiomers are, for example:
(S)-thiophene-2,5-dicarboxylic acid 2-[(1-benzofuran-2-yl-ethyl)-amide]5-hydroxyamide,
(S)-thiophene-2,5-dicarboxylic acid 2-hydroxyamide 5-{[1-(5-phenyl-isoxazol-3-yl)-ethyl]-amide},
(S)-thiophene-2,5-dicarboxylic acid 2-hydroxyamide 5-[(1-pyridin-2-yl-ethyl)-amide],
(S)-thiophene-2,5-dicarboxylic acid 2-hydroxyamide 5-[(1-furan-2-yl-ethyl)-amide],
(S)-thiophene-2,5-dicarboxylic acid 2-hydroxyamide 5-[(1-pyridin-3-yl-ethyl)-amide],
(S)-thiophene-2,5-dicarboxylic acid 2-hydroxyamide 5-{[1-(1-methyl-1H-pyrrol-3-yl)-ethyl]-amide}, or
(S)-thiophene-2,5-dicarboxylic acid 2-hydroxyamide 5-[(1-pyridin-4-yl-ethyl)-amide].

Preferred compounds of formula (I) include:
(R)-thiophene-2,5-dicarboxylic acid 2-{[1-(4-phenoxyphenyl)-ethyl]-amide}5-hydroxyamide and
(S)-thiophene-2,5-dicarboxylic acid 2-{[1-(4-phenoxyphenyl)-ethyl]-amide}5-hydroxyamide.

In another embodiment, the invention relates to a process for the stereoselective manufacture of the (R)- and (S) enantiomers of formula I, by reacting a compound of formula III

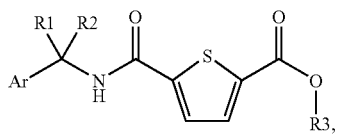

wherein R3 is a methyl group;

with an enantiomerically pure (R)- or (S)-amine of the formula III-A

Ar—C(R1)(R2)—NH$_2$     III-A, wherein Ar, R1 and R2 have the meaning defined hereinbefore, in the presence of a suitable activating agent, to give a compound of formula II

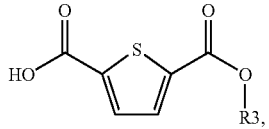

which is treated with hydroxylamine, or its hydrochloride, to give the respective enantiomerically pure compound of formula I; and if desired, transforming said compound into its pharmaceutically acceptable salt.

Compounds of formula (I), or pharmaceutically acceptable salts thereof, may be prepared by any process known to be applicable to the preparation of chemically-related compounds. Such processes, when used to prepare a thiophene hydroxamic acid derivative of the formula (I), or a pharmaceutically-acceptable salt thereof, are provided as a further feature of the invention and are illustrated by the following representative examples in which, unless otherwise stated, Ar, R1 and R2 have any of the meanings defined hereinbefore. The starting materials may be obtained by standard procedures of organic chemistry. The preparation of such starting materials is described within the accompanying non-limiting examples. Alternatively, starting materials are obtainable by analogous procedures to those illustrated which are within the ordinary skill of an organic chemist.

(a) One preferred method for the production of compounds of the formula I involves the reaction of compounds of the formula II,

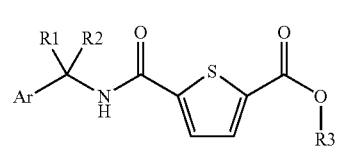

wherein Ar, R1 and R2 have the meaning defined hereinbefore and R3 is a (C1–C4)alkyl group, preferably a methyl or ethyl group, with hydroxylamine in the presence of a suitable base. The reaction is carried out in an inert solvent or diluent such as methanol or ethanol at temperatures between 0° C. and 100° C., conveniently at or near ambient temperature, and at a pH between 10 and 12. A suitable base is, for example, an alcoholate, for example, sodium methylate. Instead of generating hydroxylamine in situ, it can be released separately and can be applied as a solution in an organic solvent, as for example an alcohol like methanol or ethanol.

Compounds of formula II are prepared from compounds of the formula III wherein R3 has the meaning defined hereinbefore.

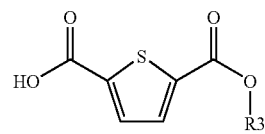

This reaction typically involves a two-step one-pot procedure. In the first step, the carboxylate of the formula III becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester formed by the reaction of the acid and a phenol such as pentafluorophenol; an active ester formed by the reaction of the acid and N-hydroxybenzotriazole; the corresponding carbonylimidazole to III formed by the reaction of the acid and N,N'-carbonyldiimidazole; an acyl azide formed by the reaction of the acid and an azide such as diphenylphosphoryl azide; an acyl cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazo lidinyl)-phosphorylchloride. The reaction is carried out between −30° C. and 60° C., conveniently at or below 0° C. In the second step, an enantiomerically pure amine of the formula Ar—C(R1)(R2)—NH₂ in which R1 and R2 have the meaning defined hereinbefore is added to the solution, at the temperature used for the activation, and the temperature is slowly adjusted to ambient temperature. An appropriate scavenger base like e.g. triethylamine, or diisopropyethlyamine may be added to the reaction mixture. These methods are well known to those skilled in the art. In principle, all methods for the synthesis of amides as used in peptide chemistry as described in e.g. Houben-Weyl, "Methoden der organischen Chemie", Vols. XV/1 and XV/2, Georg Thieme Verlag, Stuttgart, are also applicable.

Compounds of formula III are described in the literature, for example in U.S. Pat. No. 2,680,731 and J. Heterocycl. Chem. 28 (1991) 17. These monoesters are usually prepared by selective saponification of the diester or oxidation of the corresponding aldehyde, but other methods may be useful as well and are well known to those skilled in the art.

Enantiomerically pure amines of the formula Ar—C(R1)(R2)—NH2 in which R1 and R2 have the meaning defined hereinbefore are commercially available or can be prepared by standard procedures of synthetic chemistry as described e.g. in J. Am. Chem. Soc. 64 (1942) 477; J. Am. Chem. Soc. 105 (1983) 1578; or Hanano, T., et al., Bioorg. Med. Chem. Lett. 10 (2000) 881–884. Racemic amines of the formula Ar—C(R1)(R2)—NH₂ in which R1 and R2 have the meaning defined hereinbefore can be separated into their enantiomers by known procedures as, for example, enzymatic separation of racemates as described e.g. in Rasor, P., and Voss, E., Applied Catalysis A 221 (2001) 145–158, and Iglesias, L. E., et al., Tetrahedron: Asymmetry 8 (1997) 2675–2677.

(b) Another preferred method for the preparation of compounds of the formula I is the deprotection of compounds of the formula IV

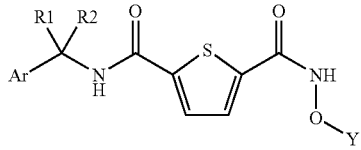

(IV)

wherein Y is a suitable protecting group and Ar, R1 and R2 have the meaning defined hereinbefore.

Compounds of the formula IV are new and included in the present invention.

Suitable protecting groups may be the benzyl-, p-methoxybenzyl-, tert.butyloxycarbonyl-, trityl-, or silyl groups such as the trimethylsilyl- or dimethyl-tert.butylsilyl-group. The reactions carried out depend on the type of the protecting group. When the protecting group is a benzyl- or p-methoxybenzyl group, the reaction carried out is a hydrogenolysis in an inert solvent such as an alcohol like methanol or ethanol, in the presence of a noble metal catalyst such as palladium on a suitable carrier such as carbon, barium sulfate, or barium carbonate, at ambient temperature and pressure. When the protecting group is the tert.butyloxycarbonyl-, trityl-, or a silyl group such as the trimethylsilyl- or dimethyl-tert.butylsilyl-group, the reaction is carried out in the presence of acids at a temperature between −20° C. and 60° C., preferably between 0° C. and ambient temperature. The acid may be a solution of hydrochloric acid in an inert solvent such as diethyl ether or dioxane, or trifluoro acetic acid in dichloromethane. When the protecting group is a silyl group such as the trimethylsilyl or dimethyl-tert.butylsilyl group, the reaction can also be carried out in the presence of a fluoride source such as sodium fluoride or tetrabutyl ammonium fluoride in an inert solvent such as dichloromethane. Not necessarily all protecting groups Y are compatible with all groups R1 or R2. In cases where the features of these groups don't allow the usage of a certain protecting group, other protecting groups Y or other methods of preparation need to be applied.

Compounds of formula IV are obtained from the reaction of compounds of formula V

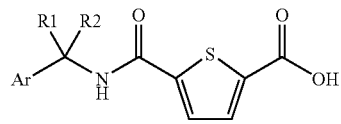

(V)

with a compound of the formula VI

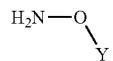

(VI)

wherein Y is a suitable protecting group as described above. This reaction typically involves a two-step one-pot procedure. In the first step, the carboxylate of the formula V becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conveniently at or below 0° C. In the second step, compound VI is added to the solution, at the temperature used for the activation, and the temperature is slowly adjusted to ambient temperature. These methods are well known to those skilled in the art. In principle, all methods for the synthesis of amides as used in peptide chemistry as described in e.g. Houben-Weyl, "Methoden der organischen Chemie", Vols. XV/1 and XV/2 are also applicable.

Compounds of the formula V are prepared from compounds of the formula II by hydrolysis. The conditions under which the hydrolysis is carried out depend on the nature of the group R3. When R3 is a methyl or ethyl group, the reaction is carried out in the presence of a base, for example, lithium hydroxide, sodium hydroxide, or potassium hydroxide in an inert solvent or diluent, for example, in methanol or ethanol. When R3 is a tert.butyl group, the reaction is carried out in the presence of an acid, for example, a solution of hydrochloric acid in an inert solvent such as diethyl ether or dioxane, or trifluoroacetic acid in dichloromethane. When R3 is a benzyl group, the reaction is carried out by hydrogenolysis in the presence of a noble metal catalyst such as palladium or platinum on a suitable carrier, such as carbon. Not necessarily all methods of hydrolysis are compatible with all groups R1 or R2. In cases where the features of these groups do not allow the usage of a certain method of hydrolysis, other methods of preparation need to be applied.

(c) Another preferred method for the preparation of compounds of the formula I is the reaction of a compound of the formula V with hydroxylamine. This reaction typically involves a two-step one-pot procedure. In the first step, the carboxylate of the formula V becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conveniently at or below 0° C. In the second step, hydroxylamine is added to the solution, at the temperature used for the activation, and the temperature is slowly adjusted to ambient temperature. These methods are well known to those skilled in the art. In principle, all methods for the synthesis of amides as used in peptide chemistry as described in e.g. Houben-Weyl, "Methoden der organischen Chemie", Vols. XV/1 and XV/2 are also applicable.

(d) Yet another preferred method for the preparation of compounds of the formula I is the synthesis of racemic compounds according to methods (a), (b), (c), or (e) applying racemic amines of the formula Ar—C(R1)(R2)—NH2 in which R1 and R2 have the meaning defined hereinbefore. The racemates can be separated into both enantiomers on either the stage of the final products or the precursors of formula II. The separation can be performed by chromatography on an analytical, semi-preparative or preparative scale using suitable optically active stationary phases with suitable eluents. Suitable optically active stationary phases include, but are not limited to, silica (e.g. ChiraSper, Merck; Chiralpak OT/OP, Baker), cellulose esters or carbamates (e.g. Chiracel OB/OY, Baker) or others (e.g. Crownpak, Daicel or Chiracel OJ-R, Baker). Other methods for the separation of enantiomers can also be applied, like the formation of diastereomeric compounds from compounds of the formula I together with other optically active compounds, e.g. camphorsulfonic acid or brucin, and separation of these diastereomeric compounds, followed by the liberation from the optically active agent.

(e) Compounds of formula I can also be prepared with methods of solid phase supported synthesis. 2,5-Thiophenedicarboxylic acid is reacted with a hydroxylamine moiety (—O—NH2) bound to a resin, e.g. a Wang resin (Wang-O—NH2 resin, supplied by EMC microcollections, Tübingen) to form a resin-bound hydroxamic acid. The second carbonic acid moiety is reacted with an amine Ar—C(R1)(R2)—NH2 by standard methods of amide bond formation as described in e.g. Houben-Weyl, "Methoden der organischen Chemie", Vols. XV/1 and XV/2. After this, the hydroxamic acid is liberated from the solid support. This can be done for example with TFA. Typically, the cleavage of the hydroxamic acids is achieved by treatment of the resin with 50% TFA in dichloromethane in the presence of triisopropyl silane at ambient temperature. The crude products can be purified by LC-MS, if necessary.

The compounds according to the present invention may exist in the form of their pharmaceutically acceptable salts. The term "pharmaceutically acceptable" or "physiologically acceptable" salt refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds. See, e.g., Ansel, H., et. al., Pharmaceutical Dosage Forms and Drug Delivery Systems, 6th ed., 1995, at pp. 196 and 1456–1457.

In another embodiment the current invention relates to pharmaceutical compositions containing a therapeutically effective amount of at least one enantiomerically pure compound of formula I with a pharmaceutically acceptable excipient and/or diluent.

The pharmaceutical compositions according to the invention may be in a form suitable for oral administration, for example as tablets, coated tablets, dragées, capsules, solutions emulsions or suspensions; for parenteral injections (including intravenous, subcutaneous, intramuscular, intravascular or infusion) as a sterile solution, suspension or emulsion; for topical administration as an ointment or cream or for rectal administration as a suppository. These pharmaceutical compositions can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions may also contain preservatives, solubilizers, stabilizers, wetting agents, emulsifiers, sweeteners, colorants, flavorants, salts for varying the osmotic pressure, buffers, masking agents or antioxidants. They may also contain additional therapeutically active substances.

A preferred pharmaceutical preparation can be obtained by using the following procedure for a tablet formulation:

| Item | Ingredients | Mg/Tablet | |
|---|---|---|---|
| 1 | Compound 1 | 25 | 100 |
| 2 | Anhydrous Lactose | 73 | 35 |
| 3 | Croscarmellose Sodium | 6 | 8 |
| 4 | Povidone K30 | 5 | 6 |
| 5 | Magnesium Stearate | 1 | 1 |
| | Total Weight | 140 | 150 |

Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.
Compound 1 is described in Example 1.

Another preferred pharmaceutical preparation is a micro-suspension of the compounds according to the invention. To obtain said micro-suspension the following materials were used:

An aqueous solution of 7.5% modified gelatine XF 20 (Braun) per injection (dissolved, filtered with a pore size of 0.45 μm and autoclaved), filters (custom made, mesh size 100 μm), filter holder, coupling, washed glass beads with a diameter of 0.25 mm and heat sterilised Retsch mills.

For the preparation of a typical batch 6244 mg of compound 1, as described in example 1, were weighted into two 50 ml bottle flasks with 30 g glass beads, dispersed with a spatulum and vortexed. Then 10 ml gelatine vehicle were added to each bottle. The bottles were vortexed, capped and wrapped in aluminium foil for light protection. The contents was milled for 14 hours at 30/s in a Retsch mill. The micro-suspension was then extracted from the beads with two layers of filter (100 μm) on a filter holder, coupled to a recipient vial by centrifugation at 400 g during two minutes and including six washing steps, to give a final volume of 130 ml.

After homogenisation, the content was determined by HPLC to be 45.7 mg/ml which corresponds to a yield of 95%. The micro-suspension was diluted with 18.6 ml to give a final concentration of 40 mg/ml. The obtained spherical, granule-like particles show diameters between 1 and 5 μm as determined by microscopy. For storage, the micro-suspension was filled into sterile vials, capped, labelled and kept at −20° C. Before use, the micro-suspension must be homogenised vigorously by vortex.

The thiophene hydroxamic acid derivative will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–100 mg/kg is employed. However the daily dose may be varied depending upon the host treated, the particular route of administration, and the severity of the illness being treated. Accordingly the optimum dosage may be determined by the practitioner who is treating any particular patient.

The anti-proliferative activity of the compounds according to this invention can be demonstrated on a human colon carcinoma cell line using a standard MTT-assay. MTT (3-(4,5-dimethylthiazol-2-yl)-2,5-diphenyl tetrazolium bromide) is widely used for the quantitative determination of cytotoxic effects or in vitro chemosensitivity of tumor cells. The assay is based on the cleavage of the yellow tetrazolium salt (MTT) to purple formazan crystals by metabolic active cells. For details, see Rubinstein, L. V., et al., J. Natl. Cancer Inst. 82 (1990) 1113.

We proceeded as follows: HT-29 cells (human colon carcinoma cell line) were cultivated in RPMI 1640, 2.5% FCS, 2 mM glutamine, 100 u/ml penicillin, 100 ug/ml streptomycin. For the assay the cells were seeded in 384 well plates, 900 cells per well, in the same medium. At the next day, the compounds (dissolved 10 mM in DMSO) were added in various concentrations ranging from 30 uM to 1.5 nM. After 5 days, the MTT assay was done mainly according to the instructions of the manufacturer (Cell proliferation kit I, MTT, from Roche Molecular Biochemicals). In brief: MTT labeling reagent was added to a final concentration of 0.5 mg/ml, added and incubated for 4 hrs at 37° C., 5% CO2. During this incubation time purple formazan crystals are formed. After addition of the solubilization solution (20% SDS in 0.02 M HCl) the plates were incubated overnight at 37° C., 5% CO2. After careful mixing, the plates were measured in Victor 2 (scanning multiwell spectrophotometer, Wallac) at 550 nm.

A decrease in number of living cells results in a decrease in the total metabolic activity in the sample. The decrease directly correlates to the amount of purple color resulting from the solubilization of the purple formazan crystals. Determination of $IC_{50}$ was done using XL-fit.

The results of this experiment are reported in Table 1 below.

TABLE 1

The reference compound is compound 3 of U.S. Pat. No. 5,369,108.

| Compounds according to this invention | $IC_{50}$ HT29 384 [μM] |
|---|---|
| Reference compound | 1.27 |
| Example 2f | 0.01 |
| Example 8e | 0.01 |
| Example 8d | 0.03 |
| Example 2e | 0.04 |
| Example 10f | 0.04 |
| Example 8f | 0.04 |
| Example 2c | 0.05 |
| Example 2i | 0.05 |
| Example 7 | 0.06 |
| Example 2g | 0.06 |
| Example 2h | 0.07 |
| Example 2d | 0.08 |
| Example 4l | 0.16 |
| Example 1 | 0.17 |
| Example 2b | 0.17 |
| Example 2a | 0.19 |
| Example 2m | 0.30 |
| Example 10d | 0.35 |
| Example 2n | 0.35 |
| Example 9 | 0.52 |
| Example 4i | 0.56 |
| Example 10e | 0.58 |
| Example 2l | 0.58 |
| Example 8c | 0.63 |

TABLE 1-continued

The reference compound is compound 3 of U.S. Pat. No. 5,369,108.

| Compounds according to this invention | IC$_{50}$ HT29 384 [μM] |
|---|---|
| Example 4n | 0.77 |
| Example 4g | 0.78 |
| Example 4a | 0.84 |
| Example 4c | 0.84 |
| Example 4d | 0.88 |
| Example 4f | 0.92 |

To further demonstrate the activity of the compounds according to this invention as HDAC inhibitors, their effect on histone deacetylase inhibition was evaluated using the following biochemical quench assay:

The function of histone deacetylase (HDAC) is the deacetylation of lysines in e.g. histone H4. A peptide of 17 amino acids derived from histone H4 was labeled with TAMRA at the C-terminus and QSY-7 at the N-terminus and was used as a substrate (TAMRA-first17 aa of histone H4-QSY7). Following deacetylation by HDAC, the enzyme Lys C is able to cleave the peptide after lysine. This results in a loss of the quench effect and a high fluorescence signal. Inhibition of HDAC by compounds results in low signals because Lys C could not cleave the substrate and the quench effect persists.

For dose response curves, 10 concentrations were diluted 1:3 starting at 30 uM. 10 ul compound dilution were put into each well of a 384 well plate. 10 ul HDAC were added (recombinant HDAC-1 purified from HEK 293 cells; enzyme activity has to be assessed for each preparation). 10 ul peptide substrate was added (1 uM final concentration, derived from 1 mM stock solution diluted 1:1000 in test buffer). After 90 min incubation at room temperature, the reaction was stopped by addition of 20 ul test buffer including 3 ug/ml Lys C and 0.075% SDS. After overnight incubation the fluorescence signal of TAMRA was measured (Victor 2 from Wallac, absorption 544 nm, emission 590 nm). The O.D. of DMSO-treated control wells is 100%, the % inhibition of compound treated wells is calculated in relation to 100%. Based on 10 concentrations a IC50 curve is generated by using XL.fit3.

Test buffer used: a mixture of 10 mM Hepes pH8, 10 mM NaCl, 10% Glycerol, 0.005% Triton X100, 0.1 mM EDTA, 0.1 mM TCEP. As plates were used 384 well plates (black, Greiner, 781077).

The results of this experiment are reported in Table 2 below.

TABLE 2

The reference compound is Compound 3 of U.S. Pat. No. 5,369,108.

| Compounds according to this invention | IC$_{50}$ HDAC quench assay [nM] |
|---|---|
| Reference compound | 12.10 |
| Example 10f | 0.58 |
| Example 4n | 0.80 |
| Example 8e | 1.08 |
| Example 2g | 1.18 |
| Example 8d | 1.26 |
| Example 2h | 1.31 |
| Example 8f | 1.33 |
| Example 2m | 1.38 |
| Example 10e | 1.39 |
| Example 7 | 1.66 |
| Example 2e | 1.73 |
| Example 4h | 1.79 |

TABLE 2-continued

The reference compound is Compound 3 of U.S. Pat. No. 5,369,108.

| Compounds according to this invention | IC$_{50}$ HDAC quench assay [nM] |
|---|---|
| Example 2i | 1.79 |
| Example 10c | 1.94 |
| Example 4i | 2.60 |
| Example 10d | 2.69 |
| Example 2n | 2.86 |
| Example 4m | 2.97 |
| Example 2l | 3.17 |
| Example 4g | 3.19 |
| Example 1 | 3.40 |
| Example 2a | 3.41 |
| Example 2c | 3.44 |
| Example 9 | 3.82 |
| Example 2d | 3.88 |
| Example 4l | 4.04 |
| Example 8c | 4.27 |
| Example 2f | 4.97 |
| Example 2b | 4.98 |

Additional data to support the activity of the compounds according to the present invention were obtained, using the following in vivo testings:

Determination of Acetylation Levels of Histone H3 in Tumor Bearing Mice

The HT-29 cell line is derived from a human colon adenocarcinoma and was obtained from ATCC and kept in an in house working cell bank for pharmacological use. Cells were cultured in RPMI1640/2 mM L-Glutamin medium supplemented with 10% heat inactivated FCS. For inoculation HT29 tumor cells are removed (Trypsin-EDTA, 50 U/mg) from culture flasks and transferred into culture medium (RPMI 1640, 10% heat inactivated FCS), washed and resuspended in sterile PBS to achieve a final cell concentration of $5 \times 10^6/100$ μl. Cell suspension was carefully mixed by regular shaking to avoid cell aggregation and filled into a 1.0 ml graded syringe. After s.c. inoculation of HT29 human colon carcinoma cells ($5 \times 10^6/100$ μl) in the right upper quarter of ventral breast region of NMRI nude mice, animals were inspected 2–3 times per week until xenografts reached a volume of roughly 1000 mm$^3$ or more, sufficient for analysis of histone acetylation. After single i.p. application of 400 mg/kg of the compound of example 1, formulated as microsuspension in 7.5% modified gelatin with 0.22% NaCl solution, the respective group of animals was sacrificed 3, 6, 12, and 24 h after dosing. Tumors were excised for analysis of acetylated histones (H3). An aliquot of tumors (ca. 200 mg) was analyzed for acetylated H3. Histones were extracted from xenografts by standardized methods (Richon, V. M., et al., PNAS 97 (2000) 10014–10019; Yoshida, M., et al., J. Biol. Chem. 265 (1990) 17174–17179), separated and acetylated H3 identified by Slot Blot and Immuno Blot techniques (SB-IB, Bio-Rad Laboratories GmbH, Munich, Germany) using anti-acetyled-H3 Pabs (UpState Biotechnology, Cat. #06-599). Histone protein was determined (Pierce Kit) and adjusted to 3 mg/ml to apply a standardized amount of 1 μg histone protein for H3 analysis in SB-IB. Quantification of acetylated H3 was performed by ECL (Enhanced Chemo Luminescence, Amersham Pharmacia, Hybond™ ECL™ Nitrocellulose membrane) measuring bioluminescence with the Lumi-Imager instrument (Roche Diagnostics). Data are expressed either as BLU/μg histone protein (BLU=Bio-Luminescence-Units), or as BLU percent versus vehicle control. After single administration of the compound of example 1, there was a marked and significant increase of acetylated H3 lasting for up to 24 h compared to the vehicle groups. The maximum acetylation was attained 6 h after dosing. A tabulated summary of the mean values and percentual changes are depicted below.

|  | vehicle 3 h | vehicle 6 h | vehicle 12 h | vehicle 24 h | example 1 3 h | example 1 6 h | example 1 12 h | example 1 24 h |
|---|---|---|---|---|---|---|---|---|
| BLU/1 µg | 12409 | 19646 | 16868 | 15215 | 57824 | 98717 | 75378 | 40965 |
| BLU % | 100 | 100 | 100 | 100 | 466 | 502 | 447 | 269 |
| P = |  |  |  |  | 0.002 | 0.002 | 0.002 | 0.041 |

Determination of Antitumor Activity in a HCT116 Xenograft Model

The HCT116 cell line (NCI line) is derived from a human colon adenocarcinoma and kept in an in house working cell bank. Cells were cultured in RPMI1640/2 mM L-glutamin medium supplemented with 10% heat inactivated FCS. For inoculation HCT116 tumor cells are removed (trypsin-EDTA, 50 U/mg) from culture flasks and transferred into culture medium (RPMI 1640, 10% heat inactivated FCS), washed and resuspended in sterile PBS to achieve a final cell concentration of $5\times10^6$/100 µl. Cell suspension was carefully mixed by regular shaking to avoid cell aggregation and filled into a 1.0 ml graded syringe. Tumor cell inoculation was performed under light anesthesia (Ethrane.) in the upper ventral quarter of right flank, i.e. between axilla of forelegs and midline region of NMRI nude male mice. In this site $5\times10^6$ HCT116 tumor cells were s.c. discharged in a volume of 100 µl PBS. All procedures were carried out under SPF conditions wearing appropriate clothings. After s.c. inoculation of tumor cells, measurable tumors developed in all animals. Mice were staged and randomized on day 10 according to the primary tumor dimensions. 21 days daily oral dosing was carried out using the compound of example 1 and compound 3 of WO 93/07148, WO 95/31977, U.S. Pat. No. 5,369,108 ('108 patent) as test article. 75 male NMRI nude mice were divided into 5 study groups. Each group consisted of 15 male animals. The individual groups were given the test article, formulated as microsuspensions in 7.5% modified gelatin with 0.22% NaCl solution, once daily by oral route over 29 days according to the following treatment scheme: 3 days treatment, 2 days drug holiday, 5 days treatment, 2 days drug holiday, 5 days treatment, 2 days drug holiday, 5 days treatment, 2 days drug holiday, 3 days treatment. The application volume was 10 ml/kg. The oral doses chosen were 50, 100, and 200 mg/kg of the compound of example 1 and 200 mg/kg of compound 3 of the '108 patent. The treatment resulted in a dose-dependent, significant tumor weight inhibition of 87%, 49%, and 40% in the 200 mg/kg, 100 mg/kg, and 50 mg/kg groups, respectively. Compound 3 of the '108 patent (200 mg/kg) showed similar results (49% tumor weight inhibition) as the 100 mg/kg treatment group of the compound of example 1.

Determination of Antitumor Activity in a PC-3 Xenograft Model

PC-3 prostate carcinoma cells were originally obtained from the NCI collection and were deposited after expansion in the Roche cell bank Penzberg. Tumor cell line was routinely cultured in RPMI 1640 Medium containing 10% FBS and 2 mM L-glutamine at 37° C. in a water-saturated atmosphere at 5% $CO_2$. Culture passage was performed with trypsin/EDTA 1× (Roche Diagnostics) splitting twice a week. Cell passage 3 was used in the present study.

At the day of cell injection, cells were harvested from culture flasks (Greiner T 75), transferred into 50 ml culture medium, washed once and resuspended in PBS. After an additional washing with PBS, the final cell titer was measured with a Neubauer-Chamber. The tumor cell suspension (PBS) was vortexed carefully (to reduce cell aggregation) and kept on ice. The cell suspension was filled into a 1.0 ml syringe. To generate primary tumors, $2\times10^6$ PC-3 tumor cells in a volume of 100 µl PBS were injected subcutaneously into the right flank of each mouse (NMRI nude mice). After s.c. inoculation of tumor cells, measurable tumors developed in all animals. Mice were staged and randomized on day 10 according to the primary tumor dimensions. 15 days daily oral dosing was carried out using the compound of example 1 and compound 3 of WO 93/07148, WO 95/31977, U.S. Pat. No. 5,369,108 as test article. 90 male NMRI nude mice were divided into 6 study groups. Each group consisted of 15 male animals. The individual groups were given the test article, formulated as microsuspensions in 7.5% modified gelatin with 0.22% NaCl solution, once daily by oral route over 19 days (3 cycles of 5 days treatment and a 2-day drug free period each). The application volume was 10 ml/kg. The oral doses chosen were 25, 50, 100, and 200 mg/kg of example 1 and 200 mg/kg of compound 3 of patent '108. The study was terminated on day 28 after tumor cell injection when the vehicle group reached the termination criteria. After 15 days of treatment, there was a dose-dependent, significant tumor weight inhibition of 51% and 81% for the 100 mg/kg and 200 mg/kg groups, respectively, compared to the vehicle group. Compound 3 of '108 patent (200 mg/kg) showed similar results (53% tumor weight inhibition) as the 100 mg/kg treatment group of the compound of example 1. Tumor weight inhibition of the 25 mg/kg and 50 mg/kg groups treated with the compound of example 1 were 15% and 36%, respectively.

Another embodiment of the present invention relates to a method of inhibiting tumor cell proliferation by inducing histone acetylation in said tumor cells by contacting said cells with a compound of formula (I).

Yet another embodiment of the present invention relates to a method of inhibiting tumor cell proliferation by inducing of histone acetylation in said tumor cell by contacting said cell with an enantiomerically pure compound of formula I.

Yet another embodiment of the present invention relates to a method for inhibiting tumor cell proliferation by induction of histone acetylation in a tumor cell, due to administring to said tumor cell an effective amount of one or more enantiomerically pure compounds of formula I. According to a further feature of this aspect of the invention there is provided a method for producing an anti-cell-proliferation effect in a warm-blooded animal, such as man, in need of such treatment which comprises administering to said animal an effective amount of an enantiomerically pure thiophene hydroxamic acid derivative as defined hereinbefore.

According to a more preferred aspect of the present invention there is provided an enantiomerically pure compound of the formula I as defined hereinbefore for use in a method of treatment of the human or animal body by therapy. It has been determined that the compounds of the present invention possess anti-cell-proliferation properties which are believed to arise from their histone deacetylase inhibitory activity. Accordingly the compounds of the present invention provide a method for treating the proliferation of malignant cells. The enantiomerically pure compounds of the present invention are useful in the treatment of cancer by providing an anti-proliferative effect, particularly in the treatment of cancers of the breast, lung, colon, rectum, stomach, prostate, bladder, pancreas and ovary. Compounds of the invention are also useful in the treatment of neoplasms of the hematopoetic and lymphatic system and solid tumors such as carcinomas and sarcomas in tissues such as the liver, kidney, prostate and pancreas.

The anti-cell-proliferation treatment defined hereinbefore may be applied as a sole therapy or may involve, in addition to the thiophene hydroxamic acid derivative of the invention, one or more other anti-tumor substances, for example those selected from, for example, mitotic inhibitors, for example vinblastine; alkylating agents, for example cisplatin, carboplatin and cyclophosphamide; inhibitors of microtubule assembly, like paclitaxel or other taxanes; antimetabolites, for example 5-fluorouracil, capecitabine, cytosine arabinoside and hydroxyurea, or, for example, intercalating antibiotics, for example adriamycin and bleomycin; immunostimulants, for example trastuzumab; DNA synthesis inhibitors, e.g. gemcitabine; enzymes, for example asparaginase; topoisomerase inhibitors, for example etoposide; biological response modifiers, for example interferon; and anti-hormones, for example antioestrogens such as tamoxifen or, for example antiandrogens such as (4'-cyano-3-(4-fluorophenylsulphonyl)-2-hydroxy-2-methyl-3'-(trifluoromethyl)-propionanilide, or other therapeutic agents and principles as described in, for example, Cancer: Principles & Practice of Oncology, Vincent T. DeVita, Jr., Samuel Hellmann, Steven A. Rosenberg; 5th ed., Lippincott-Raven Publishers, 1997. Such conjoint treatment may be achieved by way of the simultaneous, sequential or separate dosing of individual components of the treatment. According to this aspect of the invention there is provided a pharmaceutical product comprising a thiophene hydroxamic acid derivative of the formula I as defined hereinbefore and an additional anti-tumor substance as defined hereinbefore for the conjoint treatment of cancer.

The invention will now be illustrated in the following non-limiting examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany, or on ISOLUTE Flash sorbents and on ISOLUTE Flash columns obtained from Separtis, Grenzach-Wyhlen, Germany;

(iv) yields are given for illustration only and are not necessarily the maximum attainable;

(v) melting points were determined using a Mettler SP62 automatic melting point apparatus, an oil-bath apparatus or a Kofler hot plate apparatus.

(vi) the structures of the end-products of the formula I were confirmed by nuclear (generally proton) magnetic resonance (NMR) and mass spectral techniques (Micromass Platform II machine using APCI or Micromass Platform ZMD using electrospray);

(vii) intermediates were not generally fully characterized and purity was assessed by thin layer chromatography;

(viii) the following abbreviations have been used:

| | |
|---|---|
| $CH_2Cl_2$ | dichloromethane |
| $CO_2$ | carbon dioxide |
| DMF | N,N-dimethylformamide |
| DMSO | dimethylsulphoxide |
| HCl | hydrochloric acid |
| MeOH | methanol |
| rt | room temperature |
| SDS | sodium dodecylsulfate |
| TFA | trifluoro acetic acid |
| THF | tetrahydrofuran |
| mp | melting point |

Preparation Examples:

EXAMPLE 1

(R)-thiophene-2,5-dicarboxylic acid 2-hydroxyamide 5-[(1-phenyl-ethyl)-amide]

a) Synthesis of (R)-5-(1-Phenyl-ethylcarbamoyl)-thiophene-2-carboxylic acid methyl ester A suspension of 40 g (215 mmol) of methyl thiophen-2,5-dicarboxylate in thionylchloride (200 ml) is treated at reflux conditions for approx. 72 hours (end of HCl evolution). The reaction mixture is cooled-down to rt and the thionylchloride is evaporated under reduced pressure to yield the intermediate acid chloride from the starting material. A solution of (R)-1-phenylethylamine (35.5 ml, 279 mmol) and triethylamine (150 ml, 1.07 mol) in THF (320 ml) is cooled-down to −15° C. and a cold solution (−15° C.) of the acid chloride in THF (400 ml) is added slowly. Stirring is continued for 1 hour at the same temperature and after warming-up to rt for another 16 hours. The reaction mixture is filtered and the solvent is evaporated under reduced pressure. the resulting residue is dissolved in $CH_2Cl_2$ and the product is isolated after aqueous workup and recrystallisation as white solid (mp=131–33° C.) in 83% yield (52 g).

b) Synthesis of (R)-Thiophene-2,5-dicarboxylic acid 2-hydroxyamide 5-[(1-phenyl-ethyl)-amide]

The intermediate methyl ester (35 g, 120 mmol) is dissolved in a solution of hydroxylamine in MeOH (605 ml, 2M) and subsequently treated with a solution of potassium hydroxide in MeOH (105 ml, 1.15 M). The solution is stirred at rt for 16 hours, treated with dry-ice and the solvent is evaporated under reduced pressure. The solid residue is suspended in water and the pH value is adjusted to 9. The suspension is cooled-down and the precipitate is filtered, dried and purified by flash chromatography using an ethyl acetate/MeOH eluent to yield 19.7 g (56%) of the desired product as a light brown powder (mp=180° C.). Alternatively, the product can be purified by recrystallisation from MeOH.

EXAMPLE 2

According to the preparation procedure of example 1, the following thiophene hydroxamic acid derivatives of the general formula (I) have been prepared applying the according (R)-configured chiral amines:
a) (R)-thiophene-2,5-dicarboxylic acid 2-hydroxyamide 5-[(1-p-tolyl-ethyl)-amide], (mp=189° C.);
b) (R)-thiophene-2,5-dicarboxylic acid 2-{[1-(4-fluoro-phenyl)-ethyl]-amide}5-hydroxyamide, (mp=200° C.);

c) (R)-thiophene-2,5-dicarboxylic acid 2-{[1-(4-chloro-phenyl)-ethyl]-amide}5-hydroxyamide, (mp=195° C.);
d) (R)-thiophene-2,5-dicarboxylic acid 2-{[1-(4-bromo-phenyl)-ethyl]-amide}5-hydroxyamide, (mp=209° C.);
e) (R)-thiophene-2,5-dicarboxylic acid 2-hydroxyamide 5-[(1-naphthalen-1-yl-ethyl)-amide], (mp=200° C.);
f) (R)-thiophene-2,5-dicarboxylic acid 2-hydroxyamide 5-[(1-naphthalen-2-yl-ethyl)-amide], (mp=200° C.);
g) (R)-thiophene-2,5-dicarboxylic acid 2-hydroxyamide 5-[(1-phenyl-propyl)-amide], (mp=190–195° C.);
h) (R)-thiophene-2,5-dicarboxylic acid 2-hydroxyamide 5-{[1-(3-methoxy-phenyl)-ethyl]-amide}, (mp=160° C.);
i) (R)-thiophene-2,5-dicarboxylic acid 2-hydroxyamide 5-{[1-(4-methoxy-phenyl)-ethyl]-amide} (mp=195° C.);
j) (R)-thiophene-2,5-dicarboxylic acid 2-hydroxyamide 5-[(2-hydroxy-1-phenyl-ethyl)-amide] (mp=215° C.);
k) (R)-thiophene-2,5-dicarboxylic acid 2-hydroxyamide 5-[(3-hydroxy-1-phenyl-propyl)-amide];
l) (R)-thiophene-2,5-dicarboxylic acid 2-hydroxyamide 5-[(2-methoxy-1-phenyl-ethyl)-amide] (mp=192° C.);
m) (R)-thiophene-2,5-dicarboxylic acid 2-hydroxyamide 5-indan-1-ylamide, (mp=183° C.); and
n) (R)-thiophene-2,5-dicarboxylic acid 2-hydroxyamide 5-[(1,2,3,4-tetrahydro-naphthalen-1-yl)-amide], (mp=171° C.).

EXAMPLE 3

(S)-Thiophene-2,5-dicarboxylic acid 2-hydroxyamide 5-[(1-p-tolyl-ethyl)-amide]

a) Synthesis of (S)-5-(1-p-Tolyl-ethylcarbamoyl)-thiophene-2-carboxylic acid methyl ester A solution of 1.4 g (7.5 mmol) of methyl thiophen-2,5-dicarboxylate in $CH_2Cl_2$ (5 ml) is treated with 1.5 ml (18 mmol) thionylchloride and one drop of DMF and subsequently heated at 80° C. for 1 hour. The solvent and excess of thionylchloride are evaporated under reduced pressure, and the residue is dissolved in $CH_2Cl_2$ (10 ml) and treated slowly with (S)-1-(p-tolyl)ethylamine (1.0 g, 7.4 mmol) in $CH_2Cl_2$ (10 ml) and triethylamin (2 ml, 14.2 mmol). Stirring at rt is continued for 1 additional hour. The product is isolated after acidic work-up and recrystallisation as yellow solid (mp=165° C.) in 71% yield (1.6 g).

b) Synthesis of (S)-Thiophene-2,5-dicarboxylic Acid 2-hydroxyamide 5-[(1-p-tolyl-ethyl)-amide]

To a cold solution of hydroxylamine in MeOH (15 ml, 2M) are added (S)-5-(1-p-Tolyl-ethylcarbamoyl)-thiophene-2-carboxylic acid methyl ester (910 mg, 3 mmol) and subsequently another cold solution of potassium hydroxide in MeOH (4 ml, 0.75M). After warming-up to rt, the solution is stirred at that temperature for another 2 hours. The mixture is then treated with dry-ice, the precipitate is filtered-off and the filtrate is evaporated under reduced pressure to dryness. The solid residue is thoroughly washed with water, filtered, dried and recrystallized from MeOH to yield 640 mg (70%) of the desired product as a white solid (mp=189° C.).

EXAMPLE 4

According to the preparation procedure of example 3, the following thiophene hydroxamic acid derivatives of the general formula I have been prepared applying the according (S)-configured chiral amines:
a) (S)-thiophene-2,5-dicarboxylic acid 2-hydroxyamide 5-[(1-phenyl-ethyl)-amide] (mp=198° C.);
b) (S)-thiophene-2,5-dicarboxylic acid 2-{[1-(4-fluoro-phenyl)-ethyl]-amide}5-hydroxyamide, (mp=199° C.);
c) (S)-thiophene-2,5-dicarboxylic acid 2-{[1-(4-chloro-phenyl)-ethyl]-amide}5-hydroxyamide, (mp=197° C.);
d) (S)-thiophene-2,5-dicarboxylic acid 2-{[1-(4-bromo-phenyl)-ethyl]-amide}5-hydroxyamide, (mp=183° C.);
e) (S)-thiophene-2,5-dicarboxylic acid 2-hydroxyamide 5-[(1-naphthalen-1-yl-ethyl)-amide], (mp=167° C.);
f) (S)-thiophene-2,5-dicarboxylic acid 2-hydroxyamide 5-[(1-naphthalen-2-yl-ethyl)-amide], (mp=200° C.);
g) (S)-thiophene-2,5-dicarboxylic acid 2-hydroxyamide 5-[(1-phenyl-propyl)-amide], (mp=210° C.);
h) (S)-thiophene-2,5-dicarboxylic acid 2-hydroxyamide 5-{[1-(3-methoxy-phenyl)-ethyl]-amide}, (mp=170° C.);
i) (S)-thiophene-2,5-dicarboxylic acid 2-hydroxyamide 5-{[1-(4-methoxy-phenyl)-ethyl]-amide} (mp=190° C.);
j) (S)-thiophene-2,5-dicarboxylic acid 2-hydroxyamide 5-[(2-hydroxy-1-phenyl-ethyl)-amide] (mp=165° C.);
k) (S)-thiophene-2,5-dicarboxylic acid 2-hydroxyamide 5-[(3-hydroxy-1-phenyl-propyl)-amide];
l) (S)-thiophene-2,5-dicarboxylic acid 2-hydroxyamide 5-[(2-methoxy-1-phenyl-ethyl)-amide] (mp=189° C.);
m) (S)-thiophene-2,5-dicarboxylic acid 2-hydroxyamide 5-indan-1-ylamide (mp=178° C.); and
n) (S)-thiophene-2,5-dicarboxylic acid 2-hydroxyamide 5-[(1,2,3,4-tetrahydro-naphthalen-1-yl)-amide] (mp=173° C.).

EXAMPLE 5

Thiophene-2,5-dicarboxylic Acid 2-hydroxyamide 5-[(1-thiophen-2-yl-ethyl)-amide]

a) Synthesis of 5-(1-Thiophen-2-yl-ethylcarbamoyl)-thiophene-2-carboxylic acid methyl ester A solution of 500 mg (2.7 mmol) of methyl thiophen-2,5-dicarboxylate in $CH_2Cl_2$ (20 ml) is treated with 617 mg (4 mmol) 1-hydroxybenzotriazole hydrate and 772 mg (4 mmol) N'-(3-dimethylaminopropyl)-N-ethylcarbodiimid hydrochloride and stirring is continued at ambient temperature for 1 hour. 410 mg (3.2 mmol) of 1-thiophen-2-yl-ethylamine are added to the reaction mixture which is subsequently stirred at ambient temperature overnight. The product is isolated after acidic work-up and purification on silica gel as waxy solid in 84% yield (0.67 g).

b) Synthesis of Thiophene-2,5-dicarboxylic acid 2-hydroxyamide 5-[(1-thiophen-2-yl-ethyl)-amide]

To a cold solution of hydroxylamine in MeOH (5 ml, 2M) are added 5-(1-Thiophen-2-yl-ethylcarbamoyl)-thiophene-2-carboxylic acid methyl ester (300 mg, 1 mmol) and subsequently another cold solution of potassium hydroxide in MeOH (2 ml, 0.5M). After warming-up to rt, the solution is stirred at that temperature for another 3 hours. The mixture is then treated with dry-ice, the precipitate is filtered-off and the filtrate is evaporated under reduced pressure to dryness. The solid residue is thoroughly washed with water, filtered, and dried to yield 260 mg (87%) of the desired product as a white solid (mp=173° C.).

EXAMPLE 6

According to the preparation procedure of example 5, the following thiophene hydroxamic acid derivatives of the general formula I have been prepared:
a) Thiophene-2,5-dicarboxylic acid 2-[(2-dimethylamino-1-phenyl-ethyl)-amide]5-hydroxyamide;

b) Thiophene-2,5-dicarboxylic acid 2-hydroxyamide 5-[(1-phenyl-2-pyrrolidin-1-yl-ethyl)-amide];
c) Thiophene-2,5-dicarboxylic acid 2-hydroxyamide 5-[(2-morpholin-4-yl-1-phenyl-ethyl)-amide];
d) Thiophene-2,5-dicarboxylic acid 2-hydroxyamide 5-{[1-(4-trifluoromethyl-phenyl)-ethyl]-amide};
e) Thiophene-2,5-dicarboxylic acid 2-{[1-(4-tert-butyl-phenyl)-ethyl]-amide}5-hydroxyamide;
f) Thiophene-2,5-dicarboxylic acid 2-[(1,2-diphenyl-ethyl)-amide]5-hydroxyamide;
g) Thiophene-2,5-dicarboxylic acid 2-hydroxyamide 5-[(1-phenyl-pentyl)-amide];
h) Thiophene-2,5-dicarboxylic acid 2-hydroxyamide 5-[(1-phenyl-butyl)-amide];
i) Thiophene-2,5-dicarboxylic acid 2-hydroxyamide 5-[(2-methyl-1-phenyl-propyl)-amide];
j) Thiophene-2,5-dicarboxylic acid 2-hydroxyamide 5-[(3-methyl-1-phenyl-butyl)-amide];
k) Thiophene-2,5-dicarboxylic acid 2-[(1-benzofuran-2-yl-ethyl)-amide]5-hydroxyamide;
l) Thiophene-2,5-dicarboxylic acid 2-hydroxyamide 5-{[1-(5-phenyl-isoxazol-3-yl)-ethyl]-amide};
m) Thiophene-2,5-dicarboxylic acid 2-hydroxyamide 5-[(1-pyridin-2-yl-ethyl)-amide];
n) Thiophene-2,5-dicarboxylic acid 2-hydroxyamide 5-{[1-(4-methanesulfonyl-phenyl)-ethyl]-amide};
o) Thiophene-2,5-dicarboxylic acid 2-{[1-(3-amino-phenyl)-ethyl]-amide}5-hydroxyamide;
p) Thiophene-2,5-dicarboxylic acid 2-{[1-(2-amino-phenyl)-ethyl]-amide}5-hydroxyamide;
q) Thiophene-2,5-dicarboxylic acid 2-hydroxyamide 5-[(1-furan-2-yl-ethyl)-amide];
r) Thiophene-2,5-dicarboxylic acid 2-hydroxyamide 5-[(1-pyridin-3-yl-ethyl)-amide];
s) Thiophene-2,5-dicarboxylic acid 2-hydroxyamide 5-{[1-(1-methyl-1H-pyrrol-3-yl)-ethyl]-amide};
t) Thiophene-2,5-dicarboxylic acid 2-{[1-(4-ethyl-phenyl)-ethyl]-amide}5-hydroxyamide;
u) Thiophene-2,5-dicarboxylic acid 2-{[1-(4-phenoxy-phenyl)-ethyl]-amide}5-hydroxyamide;
v) Thiophene-2,5-dicarboxylic acid 2-{[1-(4-ethoxy-phenyl)-ethyl]-amide}5-hydroxyamide;
w) Thiophene-2,5-dicarboxylic acid 2-hydroxyamide 5-[(1-pyridin-4-yl-ethyl)-amide];
x) Thiophene-2,5-dicarboxylic acid 2-hydroxyamide 5-[(1-biphenyl-4-yl-ethyl)-amide];
y) Thiophene-2,5-dicarboxylic acid 2-{[1-(4-carbamoyl-phenyl)-ethyl]-amide}5-hydroxyamide;
z) Thiophene-2,5-dicarboxylic acid 2-hydroxyamide 5-({1-[4-(3-methyl-butylcarbamoyl)-phenyl]-ethyl}-amide); and
aa) Thiophene-2,5-dicarboxylic acid 2-hydroxyamide 5-{[1-(5-methyl-thiophen-2-yl)-ethyl]-amide}.

EXAMPLE 7

(R)-Thiophene-2,5-dicarboxylic Acid 2-hydroxyamide 5-[(1-thiophen-2-yl-ethyl)-amide]

The racemic compound Thiophene-2,5-dicarboxylic acid 2-hydroxyamide 5-[(1-thiophen-2-yl-ethyl)-amide] described in example 5 has been separated into both the (R) and (S) enantiomers by chromatographical separation using a CHIRACEL O7 CSP stationary phase, Chiral Technologies Europe, and a MeOH/water eluent to yield the enantiomerically enriched (R)-configured product (mp=173° C.) (determination of enantiomerical excess, purity and yield pending). Alternatively, the separation of both enantiomers can be done on the stage of 5-(1-Thiophen-2-yl-ethylcarbamoyl)-thiophene-2-carboxylic acid methyl ester applying the same stationary phase to obtain the (R)-configured ester which is subsequently converted into the final product according to the preparation procedure of example 5b.

EXAMPLE 8

According to the preparation procedure of example 7, the following thiophene hydroxamic acid derivatives of the general formula I have been prepared:
a) (R)-thiophene-2,5-dicarboxylic acid 2-[(2-dimethylamino-1-phenyl-ethyl)-amide]5-hydroxyamide;
b) (R)-thiophene-2,5-dicarboxylic acid 2-hydroxyamide 5-[(1-phenyl-2-pyrrolidin-1-yl-ethyl)-amide];
c) (R)-thiophene-2,5-dicarboxylic acid 2-hydroxyamide 5-[(2-morpholin-4-yl-1-phenyl-ethyl)-amide] (mp=88° C.);
d) (R)-thiophene-2,5-dicarboxylic acid 2-hydroxyamide 5-{[1-(4-trifluoromethyl-phenyl)-ethyl]-amide} (mp=155° C.);
e) (R)-thiophene-2,5-dicarboxylic acid 2-{[1-(4-tert-butyl-phenyl)-ethyl]-amide}5-hydroxyamide (mp=178° C.);
f) (R)-thiophene-2,5-dicarboxylic acid 2-[(1,2-diphenyl-ethyl)-amide]5-hydroxyamide (mp=190° C.);
g) (R)-thiophene-2,5-dicarboxylic acid 2-hydroxyamide 5-[(1-phenyl-pentyl)-amide];
h) (R)-thiophene-2,5-dicarboxylic acid 2-hydroxyamide 5-[(1-phenyl-butyl)-amide];
i) (R)-thiophene-2,5-dicarboxylic acid 2-hydroxyamide 5-[(2-methyl-1-phenyl-propyl)-amide];
j) (R)-thiophene-2,5-dicarboxylic acid 2-hydroxyamide 5-[(3-methyl-1-phenyl-butyl)-amide];
k) (R)-thiophene-2,5-dicarboxylic acid 2-[(1-benzofuran-2-yl-ethyl)-amide]5-hydroxyamide;
l) (R)-thiophene-2,5-dicarboxylic acid 2-hydroxyamide 5-{[1-(5-phenyl-isoxazol-3-yl)-ethyl]-amide};
m) (R)-thiophene-2,5-dicarboxylic acid 2-hydroxyamide 5-[(1-pyridin-2-yl-ethyl)-amide];
n) (R)-thiophene-2,5-dicarboxylic acid 2-hydroxyamide 5-{[1-(4-methanesulfonyl-phenyl)-ethyl]-amide};
o) (R)-thiophene-2,5-dicarboxylic acid 2-{[1-(3-amino-phenyl)-ethyl]-amide}5-hydroxyamide;
p) (R)-thiophene-2,5-dicarboxylic acid 2-{[1-(2-amino-phenyl)-ethyl]-amide}5-hydroxyamide;
q) (R)-thiophene-2,5-dicarboxylic acid 2-hydroxyamide 5-[(1-furan-2-yl-ethyl)-amide];
r) (R)-thiophene-2,5-dicarboxylic acid 2-hydroxyamide 5-[(1-pyridin-3-yl-ethyl)-amide];
s) (R)-thiophene-2,5-dicarboxylic acid 2-hydroxyamide 5-{[1-(1-methyl-1H-pyrrol-3-yl)-ethyl]-amide};
t) (R)-thiophene-2,5-dicarboxylic acid 2-{[1-(4-ethyl-phenyl)-ethyl]-amide}5-hydroxyamide;
u) (R)-thiophene-2,5-dicarboxylic acid 2-{[1-(4-phenoxy-phenyl)-ethyl]-amide}5-hydroxyamide;
v) (R)-thiophene-2,5-dicarboxylic acid 2-{[1-(4-ethoxy-phenyl)-ethyl]-amide}5-hydroxyamide;
w) (R)-thiophene-2,5-dicarboxylic acid 2-hydroxyamide 5-[(1-pyridin-4-yl-ethyl)-amide];
x) (R)-thiophene-2,5-dicarboxylic acid 2-hydroxyamide 5-[(1-biphenyl-4-yl-ethyl)-amide];
y) (R)-thiophene-2,5-dicarboxylic acid 2-{[1-(4-carbamoyl-phenyl)-ethyl]-amide}5-hydroxyamide;
z) (R)-thiophene-2,5-dicarboxylic acid 2-hydroxyamide 5-({1-[4-(3-methyl-butylcarbamoyl)-phenyl]-ethyl}-amide); and aa) (R)-thiophene-2,5-dicarboxylic acid 2-hydroxyamide 5-{[1-(5-methyl-thiophen-2-yl)-ethyl]-amide}.

EXAMPLE 9

(S)-Thiophene-2,5-dicarboxylic Acid 2-hydroxyamide 5-[(1-thiophen-2-yl-ethyl)-amide]

The racemic compound Thiophene-2,5-dicarboxylic acid 2-hydroxyamide 5-[(1-thiophen-2-yl-ethyl)-amide] described in example 6 has been separated into both the (R) and (S) enantiomers by chromatographical separation using a CHIRACEL O7 CSP stationary phase, Chiral Technologies Europe, and a MeOH/water eluent to yield the enantiomerically enriched (S)-configured product (mp=170° C.) (determination of enantiomerical excess, purity and yield pending). Alternatively, the separation of both enantiomers can be done on the stage of 5-(1-Thiophen-2-yl-ethylcarbamoyl)-thiophene-2-carboxylic acid methyl ester applying the same stationary phase to obtain the (S)-configured ester which is subsequently converted into the final product according to the preparation procedure of Example 5b.

EXAMPLE 10

According to the preparation procedure of example 9, the following thiophene hydroxamic acid derivatives of the general formula I have been prepared:
a) (S)-thiophene-2,5-dicarboxylic acid 2-[(2-dimethylamino-1-phenyl-ethyl)-amide]5-hydroxyamide;
b) (S)-thiophene-2,5-dicarboxylic acid 2-hydroxyamide 5-[(1-phenyl-2-pyrrolidin-1-yl-ethyl)-amide];
c) (S)-thiophene-2,5-dicarboxylic acid 2-hydroxyamide 5-[(2-morpholin-4-yl-1-phenyl-ethyl)-amide] (mp=97° C.);
d) (S)-thiophene-2,5-dicarboxylic acid 2-hydroxyamide 5-{[1-(4-trifluoromethyl-phenyl)-ethyl]-amide} (mp=157° C.);
e) (S)-thiophene-2,5-dicarboxylic acid 2-{[1-(4-tert-butyl-phenyl)-ethyl]-amide}5-hydroxyamide (mp=142° C.);
f) (S)-thiophene-2,5-dicarboxylic acid 2-[(1,2-diphenyl-ethyl)-amide]5-hydroxyamide (mp=189° C.);
g) (S)-thiophene-2,5-dicarboxylic acid 2-hydroxyamide 5-[(1-phenyl-pentyl)-amide];
h) (S)-thiophene-2,5-dicarboxylic acid 2-hydroxyamide 5-[(1-phenyl-butyl)-amide];
i) (S)-thiophene-2,5-dicarboxylic acid 2-hydroxyamide 5-[(2-methyl-1-phenyl-propyl)-amide];
j) (S)-thiophene-2,5-dicarboxylic acid 2-hydroxyamide 5-[(3-methyl-1-phenyl-butyl)-amide];
k) (S)-thiophene-2,5-dicarboxylic acid 2-[(1-benzofuran-2-yl-ethyl)-amide]5-hydroxyamide;
l) (S)-thiophene-2,5-dicarboxylic acid 2-hydroxyamide 5-{[1-(5-phenyl-isoxazol-3-yl)-ethyl]-amide};
m) (S)-thiophene-2,5-dicarboxylic acid 2-hydroxyamide 5-[(1-pyridin-2-yl-ethyl)-amide];
n) (S)-thiophene-2,5-dicarboxylic acid 2-hydroxyamide 5-{[1-(4-methanesulfonyl-phenyl)-ethyl]-amide};
o) (S)-thiophene-2,5-dicarboxylic acid 2-{[1-(3-amino-phenyl)-ethyl]-amide}5-hydroxyamide;
p) (S)-thiophene-2,5-dicarboxylic acid 2-{[1-(2-amino-phenyl)-ethyl]-amide}5-hydroxyamide;
q) (S)-thiophene-2,5-dicarboxylic acid 2-hydroxyamide 5-[(1-furan-2-yl-ethyl)-amide];
r) (S)-thiophene-2,5-dicarboxylic acid 2-hydroxyamide 5-[(1-pyridin-3-yl-ethyl)-amide];
s) (S)-thiophene-2,5-dicarboxylic acid 2-hydroxyamide 5-{[1-(1-methyl-1H-pyrrol-3-yl)-ethyl]-amide};
t) (S)-thiophene-2,5-dicarboxylic acid 2-{[1-(4-ethyl-phenyl)-ethyl]-amide}5-hydroxyamide;
u) (S)-thiophene-2,5-dicarboxylic acid 2-{[1-(4-phenoxy-phenyl)-ethyl]-amide}5-hydroxyamide;
v) (S)-thiophene-2,5-dicarboxylic acid 2-{[1-(4-ethoxy-phenyl)-ethyl]-amide}5-hydroxyamide;
w) (S)-thiophene-2,5-dicarboxylic acid 2-hydroxyamide 5-[(1-pyridin-4-yl-ethyl)-amide];
x) (S)-thiophene-2,5-dicarboxylic acid 2-hydroxyamide 5-[(1-biphenyl-4-yl-ethyl)-amide];
y) (S)-thiophene-2,5-dicarboxylic acid 2-{[1-(4-carbamoyl-phenyl)-ethyl]-amide}5-hydroxyamide;
z) (S)-thiophene-2,5-dicarboxylic acid 2-hydroxyamide 5-({1-[4-(3-methyl-butylcarbamoyl)-phenyl]-ethyl}-amide); and
aa) (S)-thiophene-2,5-dicarboxylic acid 2-hydroxyamide 5-{[1-(5-methyl-thiophen-2-yl)-ethyl]-amide}.

The invention claimed is:
1. The (R)- and (S) enantiomers of compounds of formula (I)

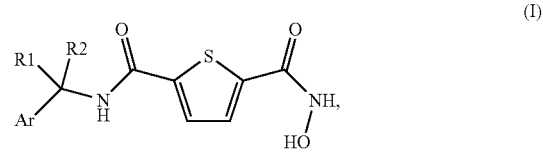

wherein
Ar is an aryl or heteroaryl group, each of which may be unsubstituted or substituted by up to three substituents selected from
halogen;
phenyl;
alkyl;
—O-alkyl;
—O-phenyl;
—O—$(CH_2)_n$—O—;
—OH;
—$NO_2$;
—$NH_2$;
—NH-alkyl;
—N(alkyl)$_2$;
—NH—C(O)-alkyl;
—$SO_2$alkyl;
—$SO_2NH_2$;
—$SO_2$NH-alkyl;
—$SO_2$N(alkyl)$_2$;
—C(O)—$NH_2$;
—C(O)—NH-alkyl;
—C(O)—N(alkyl)$_2$; or
—C(O)-alkyl;
R1 is hydrogen; or
phenyl; alkyl; or alkenyl; each of which may be unsubstituted or substituted by
halogen,
—OH,
—$NO_2$,
—$NH_2$,
—O-alkyl,
—O-aryl, —NH(alkyl),
—N(alkyl)$_2$,
morpholino,
4-methylpiperazinyl, or
aryl; or
alternatively, R1 together with the Ar-group form a tetrahydronaphthalene-, indane- or dibenzosuberane ring;
R2 is hydrogen or alkyl; and
n is 1, 2 or 3;
or a physiologically acceptable salt thereof.

2. The compound of claim 1 wherein
Ar is an aryl or a thiophen-2-yl group, each of which may be unsubstituted or substituted by up to two substituents selected from
halogen;
phenyl;
alkyl;
—O-alkyl;
—O—(CH$_2$)$_n$—O—;
—OH;
—NO$_2$;
—NH$_2$;
—NH-alkyl;
—N(alkyl)$_2$;
—NH—C(O)-alkyl;
—SO$_2$alkyl;
—SO$_2$NH$_2$;
—SO$_2$NH-alkyl;
—SO$_2$N(alkyl)$_2$;
—C(O)—NH$_2$;
—C(O)—NH-alkyl;
—C(O)—N(alkyl)$_2$; or
—C(O)-alkyl;
R1 is hydrogen;
alkyl; or
alkyl that is substituted by
halogen;
—OH;
—NO$_2$;
—NH$_2$;
—O-alkyl;
—O-aryl;
—NH(alkyl);
—N(alkyl)$_2$;
morpholino;
4-methylpiperazinyl; or
aryl;
R2 is alkyl or hydrogen; and
n is 1, 2 or 3;
or a physiologically acceptable salt thereof.

3. The compound of claim 1 selected from
(R)-thiophene-2,5-dicarboxylic acid 2-hydroxyamide 5-[(1-thiophen-2-yl-ethyl)-amide],
(R)-thiophene-2,5-dicarboxylic acid 2-hydroxyamide 5-{[1-(5-methyl-thiophen-2-yl)-ethyl]-amide}, and
(R)-thiophene-2,5-dicarboxylic acid 2-hydroxyamide 5-[(1-biphenyl-4-yl-ethyl)-amide].

4. The compound (R)-thiophene-2,5-dicarboxylic acid 2-hydroxyamide 5-[(1-phenyl-ethyl)-amide].

5. The compound of claim 1 selected from
(S)-thiophene-2,5-dicarboxylic acid 2-hydroxyamide 5-[(1-thiophen-2-yl-ethyl)-amide],
(S)-thiophene-2,5-dicarboxylic acid 2-hydroxyamide 5-{[1-(5-methyl-thiophen-2-yl)-ethyl]-amide}, and
(S)-thiophene-2,5-dicarboxylic acid 2-hydroxyamide 5-[(1-biphenyl-4-yl-ethyl)-amide].

6. The compound of formula (I) wherein
Ar is phenyl substituted by one substituent selected from
halogen;
alkyl;
—O-alkyl;
—OH;
—NH$_2$;
—NH-alkyl;
—N(alkyl)$_2$;
—NH—C(O)-alkyl;
—SO$_2$alkyl;
—SO$_2$NH$_2$;
—SO$_2$NH-alkyl;
—SO$_2$N(alkyl)$_2$;
—C(O)—NH$_2$;
—C(O)—NH-alkyl;
—C(O)—N(alkyl)$_2$; or
—C(O)-alkyl;
R1 is hydrogen or alkyl; and
R2 is hydrogen;
or a physiologically acceptable salt thereof.

7. The (R)-enantiomers according to claim 6, selected from
(R)-thiophene-2,5-dicarboxylic acid 2-hydroxyamide 5-[(1-p-tolyl-ethyl)-amide],
(R)-thiophene-2,5-dicarboxylic acid 2-{[1-(4-fluoro-phenyl)-ethyl]-amide}5-hydroxyamide,
(R)-thiophene-2,5-dicarboxylic acid 2-{[1-(4-chloro-phenyl)-ethyl]-amide}5-hydroxyamide,
(R)-thiophene-2,5-dicarboxylic acid 2-{[1-(4-bromo-phenyl)-ethyl]-amide}5-hydroxyamide,
(R)-thiophene-2,5-dicarboxylic acid 2-hydroxyamide 5-{[1-(3-methoxy-phenyl)-ethyl]-amide},
(R)-thiophene-2,5-dicarboxylic acid 2-hydroxyamide 5-{[1-(4-methoxy-phenyl)-ethyl]-amide},
(R)-thiophene-2,5-dicarboxylic acid 2-hydroxyamide 5-{[1-(4-trifluoromethyl-phenyl)-ethyl]-amide}, and
(R)-thiophene-2,5-dicarboxylic acid 2-{[1-(4-tert-butyl-phenyl)-ethyl]-amide}5-hydroxyamide.

8. The (R)-enantiomers according to claim 6 selected from
(R)-thiophene-2,5-dicarboxylic acid 2-hydroxyamide 5-{[1-(4-methanesulfonyl-phenyl)-ethyl]-amide},
(R)-thiophene-2,5-dicarboxylic acid 2-{[1-(3-amino-phenyl)-ethyl]-amide}5-hydroxyamide,
(R)-thiophene-2,5-dicarboxylic acid 2-{[1-(2-amino-phenyl)-ethyl]-amide}5-hydroxyamide,
(R)-thiophene-2,5-dicarboxylic acid 2-{[1-(4-ethyl-phenyl)-ethyl]-amide}5-hydroxyamide,
(R)-thiophene-2,5-dicarboxylic acid 2-{[1-(4-ethoxy-phenyl)-ethyl]-amide}5-hydroxyamide,
(R)-thiophene-2,5-dicarboxylic acid 2-{[1-(4-carbamoyl-phenyl)-ethyl]-amide}5-hydroxyamide, and
(R)-thiophene-2,5-dicarboxylic acid 2-hydroxyamide 5-({1-[4-(3-methyl-butylcarbamoyl)-phenyl]-ethyl}-amide).

9. The (S)-enantiomers according to claim 6 selected from
(S)-thiophene-2,5-dicarboxylic acid 2-hydroxyamide 5-[(1-p-tolyl-ethyl)-amide],
(S)-thiophene-2,5-dicarboxylic acid 2-{[1-(4-fluoro-phenyl)-ethyl]-amide}5-hydroxyamide,
(S)-thiophene-2,5-dicarboxylic acid 2-{[1-(4-chloro-phenyl)-ethyl]-amide}5-hydroxyamide,
(S)-thiophene-2,5-dicarboxylic acid 2-{[1-(4-bromo-phenyl)-ethyl]-amide}5-hydroxyamide,
(S)-thiophene-2,5-dicarboxylic acid 2-hydroxyamide 5-{[1-(3-methoxy-phenyl)-ethyl]-amide}, (S)-thiophene-2,5-dicarboxylic acid 2-hydroxyamide 5-{[1-(4-methoxy-phenyl)-ethyl]-amide}, and
(S)-thiophene-2,5-dicarboxylic acid 2-hydroxyamide 5-{[1-(4-trifluoromethyl-phenyl)-ethyl]-amide}.

10. The (S)-enantiomers according to claim 6 selected from
(S)-thiophene-2,5-dicarboxylic acid 2-{[1-(4-tert-butyl-phenyl)-ethyl]-amide}5-hydroxyamide,
(S)-thiophene-2,5-dicarboxylic acid 2-hydroxyamide 5-{[1-(4-methanesulfonyl-phenyl)-ethyl]-amide},
(S)-thiophene-2,5-dicarboxylic acid 2-{[1-(3-amino-phenyl)-ethyl]-amide}5-hydroxyamide,
(S)-thiophene-2,5-dicarboxylic acid 2-{[1-(2-amino-phenyl)-ethyl]-amide}5-hydroxyamide,
(S)-thiophene-2,5-dicarboxylic acid 2-{[1-(4-ethyl-phenyl)-ethyl]-amide}5-hydroxyamide,
(S)-thiophene-2,5-dicarboxylic acid 2-{[1-(4-ethoxy-phenyl)-ethyl]-amide}5-hydroxyamide,
(S)-thiophene-2,5-dicarboxylic acid 2-{[1-(4-carbamoyl-phenyl)-ethyl]-amide}5-hydroxyamide, and
(S)-thiophene-2,5-dicarboxylic acid 2-hydroxyamide 5-({1-[4-(3-methyl-butylcarbamoyl)-phenyl]-ethyl}-amide).

11. The compound of claim 1 wherein
Ar is phenyl;
R1 is phenyl;
alkyl; or
alkyl, substituted by
halogen;
—OH;
—NH$_2$;
—O-alkyl;
—O-aryl;
—NH(alkyl);
—N(alkyl)$_2$;
morpholinyl;
4-methylpiperazinyl; or
phenyl; and
R2 is hydrogen or alkyl;
or a physiologically acceptable salt thereof.

12. The compound of claim 11 selected from
(R)-thiophene-2,5-dicarboxylic acid 2-hydroxyamide 5-[(1-phenyl-propyl)-amide,]
(R)-thiophene-2,5-dicarboxylic acid 2-hydroxyamide 5-[(2-hydroxy-1-phenyl-ethyl)-amide],
(R)-thiophene-2,5-dicarboxylic acid 2-hydroxyamide 5-[(3-hydroxy-1-phenyl-propyl)-amide,]
(R)-thiophene-2,5-dicarboxylic acid 2-hydroxyamide 5-[(2-methoxy-1-phenyl-ethyl)-amide],
(R)-thiophene-2,5-dicarboxylic acid 2-[(2-dimethylamino-1-phenyl-ethyl)-amide]5-hydroxyamide, and
(R)-thiophene-2,5-dicarboxylic acid 2-hydroxyamide 5-[(1-phenyl-2-pyrrolidin-1-yl-ethyl)-amide].

13. The compound of claim 11 selected from
(R)-thiophene-2,5-dicarboxylic acid 2-hydroxyamide 5-[(2-morpholin-4-yl-1-phenyl-ethyl)-amide],
(R)-thiophene-2,5-dicarboxylic acid 2-[(1,2-diphenyl-ethyl)-amide]5-hydroxyamide,
(R)-thiophene-2,5-dicarboxylic acid 2-hydroxyamide 5-[(1-phenyl-pentyl)-amide],
(R)-thiophene-2,5-dicarboxylic acid 2-hydroxyamide 5-[(1-phenyl-butyl)-amide],
(R)-thiophene-2,5-dicarboxylic acid 2-hydroxyamide 5-[(2-methyl-1-phenyl-propyl)-amide], and
(R)-thiophene-2,5-dicarboxylic acid 2-hydroxyamide 5-[(3-methyl-1-phenyl-butyl)-amide].

14. The compound of claim 11 which is
(S)-thiophene-2,5-dicarboxylic acid 2-hydroxyamide 5-[(1-phenyl-ethyl)-amide].

15. The compound of claim 11 selected from
(S)-thiophene-2,5-dicarboxylic acid 2-hydroxyamide 5-[(1-phenyl-propyl)-amide],
(S)-thiophene-2,5-dicarboxylic acid 2-hydroxyamide 5-[(2-hydroxy-1-phenyl-ethyl)-amide],
(S)-thiophene-2,5-dicarboxylic acid 2-hydroxyamide 5-[(3-hydroxy-1-phenyl-propyl)-amide],
(S)-thiophene-2,5-dicarboxylic acid 2-hydroxyamide 5-[(2-methoxy-1-phenyl-ethyl)-amide],
(S)-thiophene-2,5-dicarboxylic acid 2-[(2-dimethylamino-1-phenyl-ethyl)-amide]5-hydroxyamide, and
(S)-thiophene-2,5-dicarboxylic acid 2-hydroxyamide 5-[(1-phenyl-2-pyrrolidin-1-yl-ethyl)-amide].

16. The compound of claim 11 selected from
(S)-thiophene-2,5-dicarboxylic acid 2-hydroxyamide 5-[(2-morpholin-4-yl-1-phenyl-ethyl)-amide],
(S)-thiophene-2,5-dicarboxylic acid 2-[(1,2-diphenyl-ethyl)-amide]5-hydroxyamide,
(S)-thiophene-2,5-dicarboxylic acid 2-hydroxyamide 5-[(1-phenyl-pentyl)-amide],
(S)-thiophene-2,5-dicarboxylic acid 2-hydroxyamide 5-[(1-phenyl-butyl)-amide],
(S)-thiophene-2,5-dicarboxylic acid 2-hydroxyamide 5-[(2-methyl-1-phenyl-propyl)-amide], and
(S)-thiophene-2,5-dicarboxylic acid 2-hydroxyamide 5-[(3-methyl-1-phenyl-butyl)-amide].

17. The compound of claim 1, wherein
Ar is naphthyl; and
R1 and R2 are independently selected from
hydrogen;
alkyl- or alkenyl, each of which may be unsubstituted or substituted by
alkyl;
halogen;
—OH;
—NO$_2$;
—NH$_2$;
—O-alkyl;
—O-aryl;
—NH(alkyl); or
—N(alkyl)$_2$;
or a physiologically acceptable salt thereof.

18. The compound of claim 17 selected from
(R)-thiophene-2,5-dicarboxylic acid 2-hydroxyamide 5-[(1-naphthalen-1-yl-ethyl)-amide], and
(R)-thiophene-2,5-dicarboxylic acid 2-hydroxyamide 5-[(1-naphthalen-2-yl-ethyl)-amide].

19. The compound of claim 17 selected from
(S)-thiophene-2,5-dicarboxylic acid 2-hydroxyamide 5-[(1-naphthalen-1-yl-ethyl)-amide], and
(S)-thiophene-2,5-dicarboxylic acid 2-hydroxyamide 5-[(1-naphthalen-2-yl-ethyl)-amide].

20. The compound according to claim 1, wherein
Ar and R1 together form tetrahydronaphthalenyl, indanyl, or dibenzosuberanyl, each of which may be unsubstituted or substituted by
alkyl;
halogen;
—OH;
—NO$_2$;
—NH$_2$;
—O-alkyl;
—O-aryl;

—NH(alkyl); or
—N(alkyl)$_2$; and
R2 is hydrogen;
or a physiologically acceptable salt thereof.

21. The compound of claim 20 selected from
(R)-thiophene-2,5-dicarboxylic acid 2-hydroxyamide 5-indan-1-ylamide, and
(R)-thiophene-2,5-dicarboxylic acid 2-hydroxyamide 5-[(1,2,3,4-tetrahydro-naphthalen-1-yl)-amide].

22. The compound of claim 20 selected from
(S)-thiophene-2,5-dicarboxylic acid 2-hydroxyamide 5-indan-1-ylamide, and
(S)-thiophene-2,5-dicarboxylic acid 2-hydroxyamide 5-[(1,2,3,4-tetrahydro-naphthalen-1-yl)-amide].

23. The compound according to claim 1, wherein
Ar is a heteroaryl group that may be unsubstituted or substituted by up to three substituents selected from
halogen;
phenyl;
alkyl;
—O-alkyl;
—O-phenyl;
—O—(CH$_2$)$_n$—O—;
—OH;
—NO$_2$;
—NH$_2$;
—NH-alkyl;
—N(alkyl)$_2$;
—NH—C(O)-alkyl;
—SO$_2$alkyl;
—SO$_2$NH$_2$;
—SO$_2$NH-alkyl;
—SO$_2$N(alkyl)$_2$;
—C(O)—NH$_2$;
—C(O)—NH-alkyl;
—C(O)—N(alkyl)$_2$; or
—C(O)-alkyl;
R1 is hydrogen; or
phenyl; alkyl; or alkenyl; each of which may be unsubstituted or substituted by
halogen;
—OH;
—NO$_2$;
—NH$_2$;
—O-alkyl;
—O-aryl;
—NH(alkyl);
—N(alkyl)$_2$;
morpholino;
4-methylpiperazinyl; or
aryl; or
alternatively, R1 together with the Ar-group forms a tetrahydronaphthalene-, indane- or dibenzosuberane ring;
R2 is hydrogen or alkyl; and
n is 1, 2 or 3;
or a physiologically acceptable salt thereof.

24. The compound according to claim 23, wherein
Ar is a heteroaryl group that may be unsubstituted or substituted by up to three substituents selected from
halogen;
phenyl;
alkyl;
—O-alkyl;
—O-phenyl;
—O—(CH$_2$)$_n$—O—;
—OH;
—NO$_2$;
—NH$_2$;
—NH-alkyl;
—N(alkyl)$_2$;
—NH—C(O)-alkyl;
—SO$_2$alkyl;
—SO$_2$NH$_2$;
—SO$_2$NH-alkyl;
—SO$_2$N(alkyl)$_2$;
—C(O)—NH$_2$;
—C(O)—NH-alkyl;
—C(O)—N(alkyl)$_2$; or
—C(O)-alkyl;
R1 is hydrogen;
R2 is alkyl; and
n is 1, 2 or 3;
or a physiologically acceptable salt thereof.

25. The compound according to claim 23, wherein
Ar is benzofuran-2-yl;
isoxazol-3-yl;
pyridin-2-yl;
pyridin-3-yl;
pyridin-4-yl;
furan-2-yl; or
pyrrol-3-yl;
each of which may be unsubstituted or substituted by up to two substituents selected from phenyl or alkyl;
R1 is hydrogen; and
R2 is alkyl;
or a physiologically acceptable salt thereof.

26. The compound of claim 25 selected from
(R)-thiophene-2,5-dicarboxylic acid 2-[(1-benzofuran-2-yl-ethyl)-amide]5-hydroxyamide,
(R)-thiophene-2,5-dicarboxylic acid 2-hydroxyamide 5-{[1-(5-phenyl-isoxazol-3-yl)-ethyl]-amide},
(R)-thiophene-2,5-dicarboxylic acid 2-hydroxyamide 5-[(1-pyridin-2-yl-ethyl)-amide],
(R)-thiophene-2,5-dicarboxylic acid 2-hydroxyamide 5-[(1-furan-2-yl-ethyl)-amide],
(R)-thiophene-2,5-dicarboxylic acid 2-hydroxyamide 5-[(1-pyridin-3-yl-ethyl)-amide],
(R)-thiophene-2,5-dicarboxylic acid 2-hydroxyamide 5-{[1-(1-methyl-1H-pyrrol-3-yl)-ethyl]-amide}, and
(R)-thiophene-2,5-dicarboxylic acid 2-hydroxyamide 5-[(1-pyridin-4-yl-ethyl)-amide].

27. The compound of claim 25 selected from
(S)-thiophene-2,5-dicarboxylic acid 2-[(1-benzofuran-2-yl-ethyl)-amide]5-hydroxyamide,
(S)-thiophene-2,5-dicarboxylic acid 2-hydroxyamide 5-{[1-(5-phenyl-isoxazol-3-yl)-ethyl]-amide},
(S)-thiophene-2,5-dicarboxylic acid 2-hydroxyamide 5-[(1-pyridin-2-yl-ethyl)-amide],
(S)-thiophene-2,5-dicarboxylic acid 2-hydroxyamide 5-[(1-furan-2-yl-ethyl)-amide],
(S)-thiophene-2,5-dicarboxylic acid 2-hydroxyamide 5-[(1-pyridin-3-yl-ethyl)-amide],
(S)-thiophene-2,5-dicarboxylic acid 2-hydroxyamide 5-{[1-(1-methyl-1H-pyrrol-3-yl)-ethyl]-amide}, and
(S)-thiophene-2,5-dicarboxylic acid 2-hydroxyamide 5-[(1-pyridin-4-yl-ethyl)-amide].

28. The compound of claim 1 selected from
(R)-thiophene-2,5-dicarboxylic acid 2-{[1-(4-phenoxy-phenyl)-ethyl]-amide}5-hydroxyamide, and
(S)-thiophene-2,5-dicarboxylic acid 2-{[1-(4-phenoxy-phenyl)-ethyl]-amide}5-hydroxyamide.

29. A process for the stereoselective preparation of a compound of formula (I), claim 1, comprising, a) reacting a compound of formula III

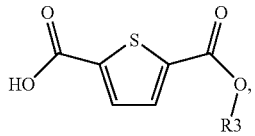

wherein

R3 is a methyl group;

with an enantiomerically pure (R)- or (S)-amine of the formula III-A

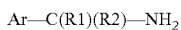

in the presence of a suitable activating agent, to give a compound of formula II

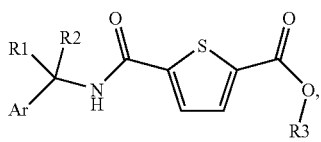

and b) treating compound II with hydroxylamine, or its hydrochloride, to give the respective enantiomerically pure compound of formula (I).

30. The method of claim 29 comprising transforming the resulting compound of formula (I) into a pharmaceutically acceptable salt.

31. A pharmaceutical composition comprising a therapeutically effective amount of a compound of formula (I), claim 1, and a pharmaceutically acceptable excipient.

32. A method of treating cancer comprising administering to a patient in need of such treatment a therapeutically effective amount of a compound of formula (I), claim 1.

33. The method of claim 32 wherein the cancer being treated is colon, breast, lung, prostate, rectal, stomach, bladder, pancreatic or ovarian cancer.

34. A compound of formula

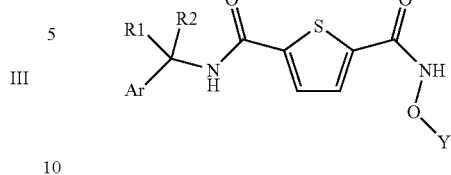

wherein
  Y is a protecting group;
  Ar is an aryl or a thiophen-2-yl group, each of which may be unsubstituted or substituted by
    halogen;
    phenyl;
    alkyl;
    —O-alkyl;
    —O—$(CH_2)_n$—O—;
    —OH;
    —$NO_2$;
    —$NH_2$;
    —NH-alkyl;
    —N(alkyl)$_2$;
    —NH—C(O)-alkyl;
    —$SO_2$alkyl;
    —$SO_2NH_2$;
    —$SO_2$NH-alkyl;
    —$SO_2$N(alkyl)$_2$;
    —C(O)—$NH_2$;
    —C(O)—NH-alkyl;
    —C(O)—N(alkyl)$_2$; or
    —C(O)-alkyl;
  R1 is hydrogen; or
    phenyl, alkyl, or alkenyl, each of which may be unsubstituted or substituted by
      halogen;
      —OH;
      —$NO_2$;
      —$NH_2$;
      —O-alkyl;
      —O-aryl;
      —NH(alkyl);
      —N(alkyl)$_2$;
      morpholino;
      4-methylpiperazinyl; or
      aryl; or
    alternatively, R1 together with the Ar-group form a tetrahydronaphthalene-, indane- or dibenzosuberane ring;
  R2 is hydrogen or alkyl; and
  n is 1, 2 or 3.

* * * * *